US010808026B2

(12) United States Patent
Imhof et al.

(10) Patent No.: US 10,808,026 B2
(45) Date of Patent: *Oct. 20, 2020

(54) MONOCLONAL OLFML-3 ANTIBODIES AND USES THEREOF

(71) Applicant: Research Development Foundation, Carson City, NV (US)

(72) Inventors: Beat A. Imhof, Geneva (CH); Marijana Miljkovic-Licina, Geneva (CH); Philippe Hammel, Geneva (CH)

(73) Assignee: Research Development Foundation, Carson City, NV (US)

( * ) Notice: Subject to any disclaimer, the term of this patent is extended or adjusted under 35 U.S.C. 154(b) by 1005 days.

This patent is subject to a terminal disclaimer.

(21) Appl. No.: 14/510,203

(22) Filed: Oct. 9, 2014

(65) Prior Publication Data

US 2015/0098947 A1    Apr. 9, 2015

Related U.S. Application Data

(60) Provisional application No. 62/018,906, filed on Jun. 30, 2014, provisional application No. 61/888,759, filed on Oct. 9, 2013.

(51) Int. Cl.
| | | |
|---|---|---|
| *C07K 16/00* | (2006.01) | |
| *A61K 39/00* | (2006.01) | |
| *A61K 39/395* | (2006.01) | |
| *C07K 16/18* | (2006.01) | |
| *G01N 33/58* | (2006.01) | |
| *C07K 16/30* | (2006.01) | |

(52) U.S. Cl.
CPC .............. *C07K 16/18* (2013.01); *C07K 16/30* (2013.01); *G01N 33/582* (2013.01); *A61K 2039/505* (2013.01); *C07K 2317/34* (2013.01); *C07K 2317/41* (2013.01); *C07K 2317/56* (2013.01); *C07K 2317/565* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| 5,859,205 A * | 1/1999 | Adair .................... C07K 16/18 |
| | | 530/387.1 |
| 9,096,662 B2 * | 8/2015 | Imhof ................ C07K 16/2896 |
| 2013/0034493 A1 * | 2/2013 | Imhof ................ C07K 16/2896 |
| | | 424/1.49 |

FOREIGN PATENT DOCUMENTS

| WO | WO 2009/055783 | 4/2009 |
| WO | WO 2010/065437 | 6/2010 |
| WO | WO 2012/170929 | 12/2012 |
| WO | WO 2013/022599 | 2/2013 |
| WO | WO 2013/072406 | 5/2013 |

OTHER PUBLICATIONS

Presentation of Bennett Celsa (Quality Assurance Specialist, TC 1600) entitled "Written Description: Antibodies" presented to the BCP Customer Partnership, Jun. 2, 2009.*
Rudikoff et al Single amino acid substitution altering antigen-binding specificity. Proc Natl Acad Sci U S A. Mar. 1982;79(6):1979-83.*
Eduardo Padlan, Anatomy of the antibody molecule. Mol Immunol. Feb. 1994;31(3):169-217.*
Paul, Fundamental Immunology, 3rd Edition, 1993, pp. 292-295.*
Brown et al. Tolerance of single, but not multiple, amino acid replacements in antibody VH CDR 2: a means of minimizing B cell wastage from somatic hypermutation? J. Immuno. May 1996, 3285-91.*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28.*
Database Geneseq, "Anti-BCMA antibody VH (BCMA-58), SEQ: 577," Accession No. BA085815, 2013.
Database Geneseq, "Mouse 22D11 anti-PCSK9 antibody VL region, SEQ ID 46," Accession No. AW047627, 2009.
Database Genseq, "Rat anti-EMAP II antibody heavy chain variable region, SEQ ID 2," Accession No. BAJ24957, 2013.
De Valence et al., "Plasma treatment for improving cell biocompatibility of a biodegradable polymer scaffold for vascular graft applications," *Eurpean Journal of PHaramaceutics and Biopharmaceutics*, 85:78-86, 2013.
Miljkovic-Licina et al., "Targeting olfactomedin-like 3 inhibits tumor growth by impairing angiogenesis and pericyte coverage," *Molecular Cancer Therapeutics*, 11(12):2588-2599, 2012.
PCT International Search Report and Written Opinion issued in International Application No. PCT/US2014/059801, dated Jan. 23, 2015.
Rodríguez-Sánchez et al., "Olfactomedin-like 3 (OLFML3 gene expression in baboon and human ocular tissues: cornea, lens, uvea, and retina," *Journal of Medical Primatology*, 42(3):105-111, 2013.
Singh et al., "Delivery of VEGF u sing collagen-coated polycaprolactone scaffolds stimulate angiogenesis," *J. Biomed. Mater. Res. A.*, 100(3):720-727, 2012.

(Continued)

*Primary Examiner* — Maher M Haddad

(74) *Attorney, Agent, or Firm* — Parker Highlander PLLC

(57) ABSTRACT

Provided herein are monoclonal antibodies against Olfml-3. In some aspects, methods for treating angiogenesis-related conditions, such as cancer, are provided comprising administering an Olfml-3-binding antibody of the embodiments.

15 Claims, 6 Drawing Sheets

Specification includes a Sequence Listing.

(56) References Cited

OTHER PUBLICATIONS

Tomarev et al., "Olfactomedin domain-containing proteins: possible mechanisms of action and functions in normal development and pathology," *Molecular Neurobiology*, 40(2): 122-138, 2009.

Torres et al., "Proteome profiling of cancer-associated fibroblasts identifies novel proinflammatory signature and prognostic markers for colorectal cancer," *Clinical Cancer Research*, 19(21):6006-6019, 2013.

Walpoth et al., "Enhanced intimal thickening of expanded polytetrafluoroethylene grafts coated with fibrin or fibrin-releasing vascular endothelial growth factor in the pig carotid artery interposition model," *J Thorac Cardiovasc Surg*, 133(5):1163-1170, 2007.

* cited by examiner

FIG. 1A-B

MONOCLONAL OLFML-3 ANTIBODIES AND USES THEREOF

This application claims the benefit of U.S. Provisional Patent Application Nos. 61/888,759, filed Oct. 9, 2013, and 62/018,906, filed on Jun. 30, 2014, each of which is incorporated herein by reference in its entirety.

INCORPORATION OF SEQUENCE LISTING

The sequence listing that is contained in the file named "CLFR.P0410US_ST25.txt", which is 11 KB (as measured in Microsoft Windows®) and was created on Oct. 3, 2014, is filed herewith by electronic submission and is incorporated by reference herein.

BACKGROUND OF THE INVENTION

1. Field of the Invention

The present invention relates generally to the field of oncology. More particularly, it concerns monoclonal antibodies against Olfml-3 and methods for their use in treating angiogenesis-related conditions.

2. Description of Related Art

Angiogenesis is a multi-step cellular process of capillary sprouting and formation of neo-vasculature from preexisting blood vessels. The complex process involves disassembly of endothelial junctions, followed by endothelial cells detachment, proliferation and migration as well as subsequent re-establishment of intercellular and cell-matrix contact. As such it requires coordinated actions of a variety of vascular cell adhesion molecules and growth factors originating from endothelial cells themselves or neighboring mural cells. Indeed, angiogenesis is a tightly tuned process regulated by pro- and anti-angiogenic factors (Folkman, 1995).

Numerous studies have demonstrated that excessive angiogenesis influences significantly various disease states including tumor growth, ischemic cardiovascular pathologies or chronic inflammatory diseases (Carmeliet, 2003; Carmeliet, 2005; Gariano and Gardner, 2005).

From vascular mediated pathologies, tumor-associated angiogenesis is the most extensively studied. It was first postulated that tumors cannot grow further than a size of 2-3 mm$^3$ in the absence of neovascularization (Folkman, 1971). Therefore, angiogenesis is a prerequisite for tumor growth and blocking this process can prevent further proliferation of tumor cells. Furthermore, prevention of angiogenesis targets normal tissue and does not escape therapy by mutagenesis as seen with tumor cells. It is thus expected that anti-angiogenic therapy be better sustained in keeping tumor growth under control than any other treatment directly addressing tumor cells. Despite the fact that vascular endothelial cell growth factor (VEGF), fibroblast growth factor (FGF) and other pro-angiogenic molecules are indispensable for vessel formation (Hanahan, 1997; Yancopoulos et al., 2000), the complete molecular and cellular mechanisms governing tumor-associated angiogenesis are poorly understood.

In addition, diseases complicated by vascular leakage and/or neovascularization in the eye are responsible for the vast majority of visual morbidity and blindness in developed countries. Retinal neovascularization occurs in ischemic retinopathies such as diabetic retinopathy and is a major cause of visual loss in working age patients (Klein et al., 1984). Choroidal neovascularization occurs as a complication of age-related macular degeneration and is a major cause of visual loss in elderly patients (Ferris et al., 1984). Improved treatments are needed to reduce the high rate of visual loss, and their development is likely to be facilitated by greater understanding of the molecular pathogenesis of ocular neovascularization.

In clinical trials, beneficial effects of anti-angiogenic drugs were so far reached with antibodies against VEGF in the context of colon and breast carcinomas. However, it was less successful with other tumors for which alternate factors may be involved. Thus, other molecules involved in angiogenesis should be identified and used alone or in combination with the growth factors. Targeting novel vascular molecules expressed and/or secreted by angiogenic endothelial cells represent an additional avenue.

SUMMARY OF THE INVENTION

In accordance with certain aspects of the present disclosure, there are provided monoclonal antibodies, or fragments thereof, that bind to Olfml-3 and inhibit the activity of Olfml-3 in angiogenesis. Thus, in some embodiments, there is provided an isolated or recombinant monoclonal antibody that specifically binds to an Olfml-3 polypeptide. In certain aspects, an antibody competes for the binding of an Olfml-3 polypeptide with a 46A9BO, 9F8BO or Z14A7 monoclonal antibody. Preferred antibodies compete for binding of the Olfml-3 polypeptide with the 46A9BO monoclonal antibody. In certain aspects, the antibody may comprise all or part of the heavy chain variable region and/or the light chain variable region of the 46A9BO, 9F8BO or Z14A7 monoclonal antibodies. In a further aspect, the antibody may comprise an amino acid sequence that corresponds to a first, second, and/or third complementarity determining region (CDR) from the light variable and/or heavy variable chain of the monoclonal antibodies of the present embodiments.

Thus, in certain aspects, an isolated or recombinant antibody of the embodiments comprises CDR sequences at least 80%, 90% or 95% identical to the CDR regions of the 46A9BO, 9F8BO or Z14A7 heavy and light chain amino acid sequences. In further aspects, an antibody comprises CDR regions identical to the 46A9BO, 9F8BO or Z14A7 CDRs, except for one or two amino acid substitutions, deletions or insertions at one, two, three or more of the CDRs. For example, the antibody can comprise CDRs wherein the CDR sequences comprise 1 or 2 amino acid substitutions in the VH CDR1, VH CDR2, VH CDR3, VL CDR1, VL CDR2 and/or VL CDR3 relative to the CDRs of a 46A9BO, 9F8BO or Z14A7 monoclonal antibody. Thus, in some specific aspects, an antibody of the embodiments comprises (a) a first VH CDR at least 80% identical to VH CDR1 of 46A9BO (SEQ ID NO: 7), or Z14A7 (SEQ ID NO: 13); (b) a second VH CDR at least 80% identical to VH CDR2 of 46A9BO (SEQ ID NO: 8), or Z14A7 (SEQ ID NO: 14); (c) a third VH CDR at least 80% identical to VH CDR3 of 46A9BO (SEQ ID NO: 9), or Z14A7 (SEQ ID NO: 15); (d) a first VL CDR at least 80% identical to VL CDR1 of 46A9BO (SEQ ID NO: 10), or Z14A7 (SEQ ID NO: 16); (e) a second VL CDR at least 80% identical to VL CDR2 of 46A9BO (SEQ ID NO: 11), or Z14A7 (SEQ ID NO: 17); and (f) a third VL CDR at least 80% identical to VL CDR3 of 46A9BO (SEQ ID NO: 12), or Z14A7 (SEQ ID NO: 18). In a further aspect, an antibody of the embodiments comprises (a) a first VH CDR at least 80% identical to VH CDR1 of 9F8BO (SEQ ID NO: 21); (b) a second VH CDR at least 80% identical to VH CDR2 of 9F8BO (SEQ ID NO: 22); (c) a third VH CDR at least 80% identical to VH CDR3 of 9F8BO (SEQ ID NO: 23); (d) a first VL CDR at least 80% identical to VL CDR1 of 9F8BO (SEQ ID NO: 24); (e) a second VL CDR at least 80% identical to VL CDR2 of 9F8BO (SEQ ID NO: 25; and (f) a third VL CDR at least 80% identical to VL CDR3 of 9F8BO (SEQ ID NO: 26).

In further aspects, an isolated or recombinant antibody comprises a first VH, a second VH, a third VH, a first VL, a second VL, and a third VL CDR sequence at least 80%, 85%, 90%, or 95% identical to the corresponding CDR sequence of monoclonal antibody 46A9BO, which are represented by SEQ ID NOs: 7, 8, 9, 10, 11, and 12, respectively. In one aspect, the isolated antibody comprises CDR sequences that are identical to the CDR sequences of monoclonal antibody 46A9BO. In further aspects, the antibody is an IgG2b antibody.

In another aspect, the isolated antibody comprises a VH domain at least about 80%, 85%, 90%, or 95% identical to the VH domain of 46A9BO (SEQ ID NO: 1) and a VL domain at least about 80%, 85%, 90%, or 95% identical to the VL domain of 46A9BO (SEQ ID NO: 2). In further aspects, the isolated antibody comprises VH and VL domains identical to those of monoclonal antibody 46A9BO.

In still further aspects, an isolated or recombinant antibody comprises a first VH, a second VH, a third VH, a first VL, a second VL, and a third VL CDR sequence at least 80%, 85%, 90%, or 95% identical to the corresponding CDR sequence of monoclonal antibody 9F8BO, which are represented by SEQ ID NOs: 21, 22, 23, 24, 25, and 26, respectively. In one aspect, the isolated antibody comprises CDR sequences that are identical to the CDR sequences of monoclonal antibody 9F8BO. In further aspects, the antibody is an IgG2b antibody.

In yet another aspect, the isolated antibody comprises a VH domain at least about 80%, 85%, 90%, or 95% identical to the VH domain of 9F8BO (SEQ ID NO: 19) and a VL domain at least about 80%, 85%, 90%, or 95% identical to the VL domain of 9F8BO (SEQ ID NO: 20). In further aspects, the isolated antibody comprises VH and VL domains identical to those of monoclonal antibody 9F8BO.

In still further aspects, the isolated or recombinant antibody comprises a first VH, a second VH, a third VH, a first VL, a second VL, and a third VL CDR sequence at least 80%, 85%, 90%, or 95% identical to the corresponding CDR sequence of monoclonal antibody Z14A7, which are represented by SEQ ID NOs: 13, 14, 15, 16, 17, and 18, respectively. In one aspect, the isolated antibody comprises CDR sequences that are identical to the CDR sequences of monoclonal antibody Z14A7. In further aspects, the antibody is an IgG2c antibody.

In another aspect, the isolated antibody comprises a VH domain at least about 80%, 85%, 90%, or 95% identical to the VH domain of Z14A7 (SEQ ID NO: 3) and a VL domain at least about 80%, 85%, 90%, or 95% identical to the VL domain of Z14A7 (SEQ ID NO: 4). In some aspects, the isolated antibody comprises VH and VL domains identical to those of monoclonal antibody Z14A7.

In some aspects, an antibody of the embodiments may be an IgG (e.g., IgG1, IgG2, IgG3 or IgG4), IgM, IgA, or an antigen binding fragment thereof. In further aspects, the antibody may be a Fab', a F(ab')2 a F(ab')3, a monovalent scFv, a bivalent scFv, or a single domain antibody. In some cases, the antibody may be a human, humanized, or de-immunized antibody. In a further aspect, the isolated antibody is the Z14A7, 9F8BO or 46A9BO antibody.

In certain aspects, an antibody (or fragment thereof) of the embodiments is a glycosylated antibody (e.g., having a mammalian glycosylation pattern). In some aspects, the antibody is a deglycosylated antibody (e.g., an enzymatically treated antibody or an antibody produced in bacteria) or has non-mammalian glycosylation (e.g., an antibody produced in yeast or insect cells).

In some embodiments, there is provided an isolated polynucleotide molecule comprising nucleic acid sequence encoding an antibody or a polypeptide comprising an antibody $V_H$ or $V_L$ domain disclosed herein.

In further embodiments, a host cell is provided that produces a monoclonal antibody or recombinant polypeptide of the embodiments. In some aspects, the host cell is a mammalian cell, a yeast cell, a bacterial cell, a ciliate cell, or an insect cell. In certain aspects, the host cell is a hybridoma cell.

In still further embodiments, there is provided a method of manufacturing an antibody of the present embodiments comprising expressing one or more polynucleotide molecule(s) encoding a $V_L$ or $V_H$ chain of an antibody disclosed herein in a cell and purifying the antibody from the cell.

In additional embodiments, there are provided pharmaceutical compositions comprising an antibody or antibody fragment as discussed herein. Such a composition further comprises a pharmaceutically acceptable carrier and may or may not contain additional active ingredients Thus, in some aspects (e.g., for medical or clinical application), an antibody or fragment may be attached to an agent to be targeted to an Olfml-3-expressing cell. The agent may be a cytotoxic agent, a cytokine, an anti-angiogenic agent, a chemotherapeutic agent, a diagnostic agent, an imaging agent, a radioisotope, a pro-apoptosis agent, an enzyme, a hormone, a growth factor, a peptide, a protein, an antibiotic, an antibody, a Fab fragment of an antibody, an imaging agent, an antigen, a survival factor, an anti-apoptotic agent, a hormone antagonist, a virus, a bacteriophage, a bacterium, a liposome, a microparticle, a magnetic bead, a microdevice, a cell, a nucleic acid or an expression vector.

There may also be provided a pharmaceutical composition comprising one or more of the antibodies or fragments described above in a pharmaceutically acceptable carrier, for example, a pharmaceutical composition comprising an antibody or fragment and a pharmaceutically acceptable carrier.

It is contemplated that the Olfml-3 antibodies or fragments or the composition of the present invention described above may be used in the treatment of any disease or disorder in which angiogenesis plays a role, which will be referred to generally as an angiogenesis-related condition. It is contemplated that the invention will find applicability in any such disorder in humans or animals. Exemplary angiogenesis-related conditions include cancer, ocular neovascularization, arterio-venous malformations, coronary restenosis, peripheral vessel restenosis, glomerulonephritis, rheumatoid arthritis, ischemic cardiovascular pathologies, chronic inflammatory diseases, etc.

In the case of cancer, exemplary angiogenic cancers include angiogenic breast cancer, lung cancer, prostate cancer, ovarian cancer, brain cancer, liver cancer, cervical cancer, colorectal cancer, renal cancer, skin cancer, head and neck cancer, bone cancer, esophageal cancer, bladder cancer, uterine cancer, lymphatic cancer, stomach cancer, pancreatic cancer, testicular cancer, lymphoma, or leukemia. Ocular neovascularization disorders include macular degeneration (e.g., age-related macular degeneration (AMD), corneal graft rejection, corneal neovascularization, retinopathy of prematurity (ROP) and diabetic retinopathy.

Certain embodiments are directed to an antibody or recombinant polypeptide composition comprising an isolated and/or recombinant antibody or polypeptide that specifically binds Olfml-3. In certain aspects the antibody or polypeptide has a sequence that is, is at least, or is at most 80, 85, 90, 95, 96, 97, 98, 99, or 100% identical (or any range derivable therein) to all or part of any monoclonal antibody provided herein. In still further aspects the isolated and/or recombinant antibody or polypeptide has, has at least, or has at most 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more contiguous amino acids from any of the sequences provided herein (e.g., SEQ ID NO:s 1, 2, 3, 4, 19 or 20) or a combination of such sequences.

In still further aspects, an antibody or polypeptide of the embodiments comprises one or more amino acid segments of the any of the amino acid sequences disclosed herein. For example, the antibody or polypeptide can comprise 1, 2, 3, 4, 5, 6, 7, 8, 9, 10 or more amino acid segments comprising about, at least or at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 amino acids in length, including all values and ranges there between, that are at least 80, 85, 90, 95, 96, 97, 98, 99, or 100% identical to any of the amino acid sequences disclosed herein. In certain aspects the amino acid segment(s) are selected from one of the amino acid sequences of an Olfml-3-binding antibody as provided in Table 1 (e.g., SEQ ID NO:s 1, 2, 3, 4, 19 or 20).

In yet further aspects, an antibody or polypeptide of the embodiments comprises an amino acid segment that is at least 80, 85, 90, 95, 96, 97, 98, 99, or 100% identical (or any range derivable therein) to a V, VJ, VDJ, D, DJ, J or CDR domain of a Olfml-3-binding antibody (as provided in Table 1). For example, a polypeptide may comprise 1, 2 or 3 amino acid segment that are at least 80, 85, 90, 95, 96, 97, 98, 99, or 100% identical (or any range derivable therein) to CDRs 1, 2, and/or 3 an Olfml-3-binding antibody as provided in Table 1.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A: Nine-day-old LLC1 tumors in mice treated with rat IgG2B (isotype control), 9F8BO (anti-Olfml-3B) or 46A9BO (anti-Olfml-3B) antibodies. Bar corresponds to 1 cm. FIG. 1B: Reduced tumor weight in mice treated with 9F8BO (anti-Olfml-3B) and 46A9BO (anti-Olfml-3B) antibodies compared with control IgG2B-treated tumors. Error bars represent SEM (1 experiment; 5 mice/group; 2 tumors/mouse). *P<0.05.

DESCRIPTION OF ILLUSTRATIVE EMBODIMENTS

Figure 1:
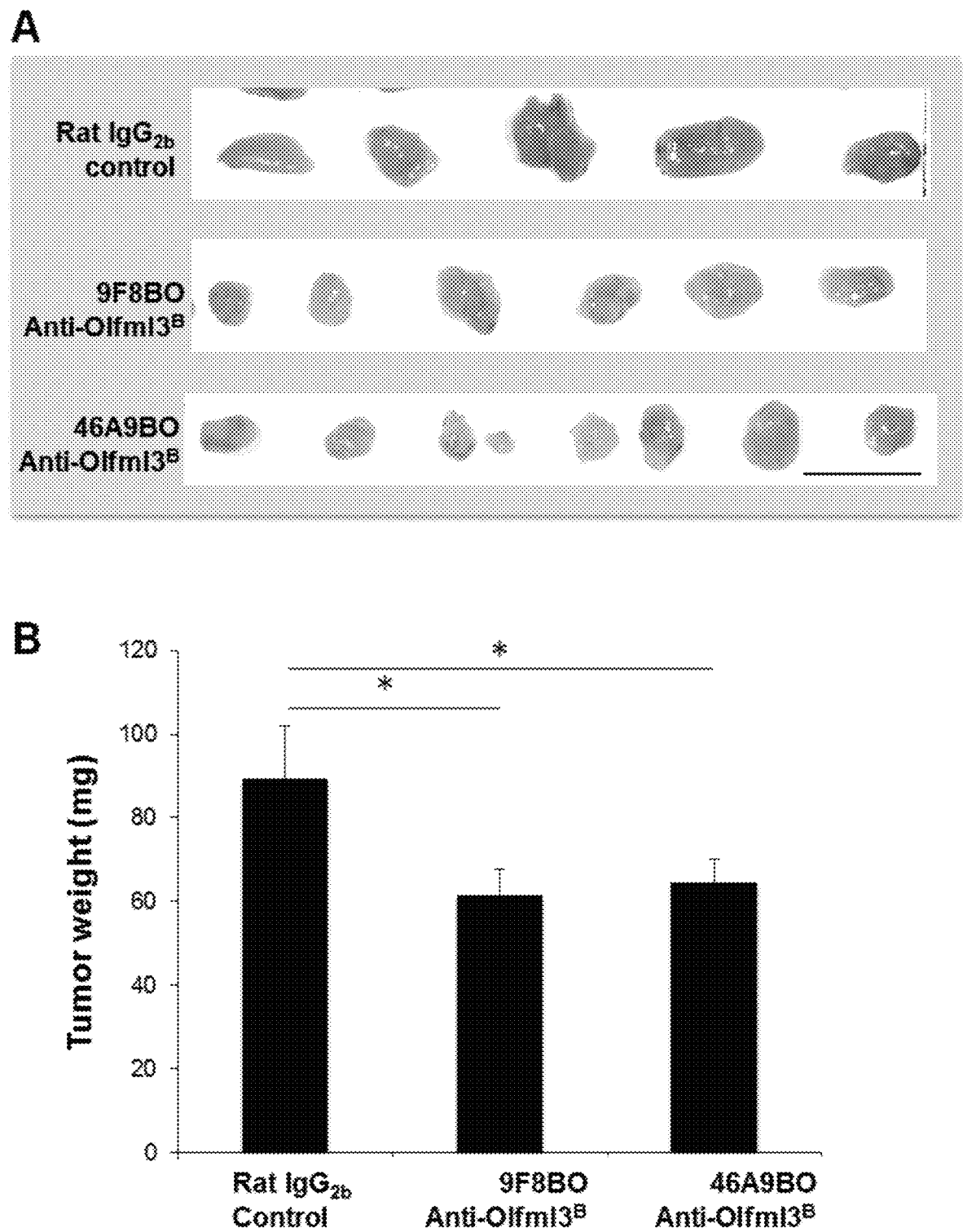
FIG. 1A-B. Inhibitory effects of rat monoclonal antibodies against human Olfml3 on tumor growth.

The present embodiments are based, in part, on the role of Olfml-3 as an angiogenesis modulator. Aspects of the present embodiments can be used to prevent or treat a disease or disorder associated with Olfml-3-mediated angiogenesis. Functioning of Olfml-3 may be reduced by a monoclonal anti-Olfml-3 antibody. In certain aspects, the present embodiments provide compositions and methods of delivery of a monoclonal antibody specific for Olfml-3 to treat angiogenesis-related disease, such as cancer. Further embodiments and advantages of the invention are described below.

I. OLFML-3

Olfactomedin-like protein 3 (Olfml-3) is a protein that in humans is encoded by the OLFML3 gene. Previously, the inventors used the t.End.1V$^{high}$ angiogenic and t.End.1V$^{low}$ resting cell lines to identify novel molecules differentially expressed and associated with angiogenesis. Among the identified angiogenesis-associated genes, they identified the mouse Olfml-3 gene (olfactomedin-like 3) (synonyms: mONT3, HNOEL-iso, hOLF44).

Some olfactomedin family members are implicated in developmental processes where they play regulatory roles, such as tiarin (Tsuda et al., 2002), pDP4 (Rosenbauer et al., 2004), and noelin (Moreno and Bronner-Fraser, 2005; Barembaum et al., 2000). Gain-of-function studies have shown that Olfml-3 (mONT3) exhibits a dorsalizing effect, as shown for tiarin, when over-expressed in Xenopus embryos (Ikeya et al., 2005), suggesting its activity in Xenopus ectodermal patterning. Recently it was shown that Xenopus ONT1 is a key molecule for fine-tuning of the Chordin/bone morphogenetic protein (BMP) system, where it acts as a secreted scaffold for the B1TP-mediated degradation of chordin (Harland, 2008; Inomata et al., 2008; Sakuragi et al., 2006). This suggests that Olfml-3 may serve as scaffold for different enzymes and substrates (Tomarev and Nakaya, 2009). All these data from disease states to developmental events underline the importance of understanding the functions of olfactomedin domain-containing proteins.

Identified by phylogenetic analysis, the human hOLF44 gene encodes for a secreted glycoprotein belonging to the Olfactomedin/Noelin/Tiarin family. Along with mONT2 (olfactomedin-like 1) and chick cONT1, the mouse Olfml-3 gene belongs to a novel, uncharacterized olfactomedin-like (ONT) subfamily of secreted molecules (Ikeya et al., 2005), including mONT3, rONT3, hONT3, cONT1, mONT2, rONT2, and hONT2. This secreted glycoprotein contains a putative signal peptide at the N-terminus, a coiled-coil domain in the middle of the sequence and an olfactomedin-like (OLF) domain at the C-terminus (Zeng et al., 2004). This molecule is involved in the formation of extracellular matrix (ECM) around olfactory neurons (Snyder et al., 1991; Yokoe and Anholt, 1993) and has regulatory roles in vertebrate neural development (Barembaum et al., 2000; Tsuda et al., 2002).

The highest level of human Olfml-3 (hOLF44) mRNA expression was found in placenta, but also in liver and heart, though at lower expression levels (Zeng et al., 2004). Endogenous hOLF44 was found in the extracellular space surrounding syncytiotrophoblastic cells on the fetal side of human term placenta, demonstrating that the molecule was secreted (Zeng et al., 2004). Tagged recombinant hOLF44 protein enriched in perinuclear regions of COS-7 cells, most likely in the endoplasmic reticulum providing evidence that it may take the classical secretory pathway (Zeng et al., 2004). These findings suggest a role for human Olfml-3 as a component associated to extracellular matrix (ECM) possibly implicated in matrix-related placental and embryonic development or similar processes (Zeng et al., 2004).

The rat orthologue of the human Olfml-3 (the rat HNOEL-iso) gene was found to be expressed in iris, sclera, the trabecular meshwork of the retina and the optic nerve (Ahmed et al., 2004). Expression of the mouse counterpart of the human Olfml-3 (mONT3) gene was detected very early during embryogenesis: firstly, in the proximal regions of the alantois, subsequently in the presumptive lateral mesoderm plate and then in the CNS and heart on embryonic day E 8.5 (Ikeya et al., 2005). The mONT-3 knock-out mice (male and female) were found to be viable, normal and fertile, suggesting that mONT3 is dispensable for normal embryogenesis and compensated by other family members (Ikeya et al., 2005). Moreover, gain-of-function studies showed mONT3 exhibits a dorsalizing effect when over-expressed in Xenopus embryos (Ikeya et al., 2005) suggesting a role in embryonic patterning.

II. THERAPEUTIC ANTIBODIES

In certain embodiments, antibodies or fragments thereof that bind to at least a portion of Olfml-3 protein and inhibit Olfml-3 activity in angiogenesis and their associated use in treatment of diseases are contemplated. As used herein, the term "antibody" is intended to refer broadly to any immunologic binding agent, such as IgG, IgM, IgA, IgD, and IgE as well as polypeptides comprising antibody CDR domains that retain antigen binding activity. The antibody may be selected from the group consisting of a chimeric antibody, an affinity matured antibody, a humanized antibody, and a human antibody. Preferably, the anti-Olfml-3 antibody is a humanized antibody. By known means and as described herein, polyclonal or monoclonal antibodies, antibody fragments, and binding domains and CDRs (including engineered forms of any of the foregoing) may be created that are specific to Olfml-3 protein, one or more of its respective epitopes, or conjugates of any of the foregoing, whether such antigens or epitopes are isolated from natural sources or are synthetic derivatives or variants of the natural compounds.

In one embodiment, the antibody is a chimeric antibody, for example, an antibody comprising antigen binding sequences from a non-human donor grafted to a heterologous non-human, human or humanized sequence (e.g., framework and/or constant domain sequences). In one embodiment, the non-human donor is a rat. In one embodiment, an antigen binding sequence is synthetic, e.g., obtained by mutagenesis (e.g., phage display screening, etc.). In one embodiment, a chimeric antibody of the invention has murine V regions and human C regions. In one embodiment, the murine light chain V region is fused to a human kappa light chain. In one embodiment, the murine heavy chain V region is fused to a human IgG1 C region.

Examples of antibody fragments suitable for the present invention include, without limitation: (i) the Fab fragment, consisting of VL, VH, CL and CH1 domains; (ii) the "Fd" fragment consisting of the VH and CH1 domains; (iii) the "Fv" fragment consisting of the VL and VH domains of a single antibody; (iv) the "dAb" fragment, which consists of a VH domain; (v) isolated CDR regions; (vi) F(ab')2 fragments, a bivalent fragment comprising two linked Fab fragments; (vii) single chain Fv molecules ("scFv"), wherein a VH domain and a VL domain are linked by a peptide linker that allows the two domains to associate to form a binding domain; (viii) bi-specific single chain Fv dimers (see U.S. Pat. No. 5,091,513) and (ix) diabodies, multivalent or multispecific fragments constructed by gene fusion (U.S. Patent App. Pub. 20050214860). Fv, scFv or diabody molecules may be stabilized by the incorporation of disulfide bridges linking the VH and VL domains. Minibodies comprising a scFv joined to a CH3 domain may also be made (Hu et al., 1996).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

Animals may be inoculated with an antigen, such as an Olfml-3 protein or peptide, in order to produce antibodies specific for an Olfml-3 protein or peptides. Frequently an antigen is bound or conjugated to another molecule to enhance the immune response. As used herein, a conjugate is any peptide, polypeptide, protein or non-proteinaceous substance bound to an antigen that is used to elicit an immune response in an animal. Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest.

A monoclonal antibody is a single species of antibody wherein every antibody molecule recognizes the same epitope because all antibody producing cells are derived from a single B-lymphocyte cell line. The methods for generating monoclonal antibodies (MAbs) generally begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and may provide certain advantages. Mice (e.g., BALB/c mice) are routinely used and generally give a high percentage of stable fusions.

Hybridoma technology involves the fusion of a single B lymphocyte from a mouse previously immunized with an Olfml-3 antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced.

Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent and human amino acid sequences. In "humanized" monoclonal antibodies, only the hypervariable CDR is derived from mouse monoclonal antibodies, and the framework regions are derived from human amino acid sequences. It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

It is possible to create engineered antibodies, using monoclonal and other antibodies and recombinant DNA technology to produce other antibodies or chimeric molecules that retain the antigen or epitope specificity of the original antibody, i.e., the molecule has binding domain. Such techniques may involve introducing DNA encoding the immunoglobulin variable region or the CDRs of an antibody to the genetic material for the framework regions, constant regions, or constant regions plus framework regions, of a different antibody. See, for instance, U.S. Pat. Nos. 5,091,513, and 6,881,557, which are incorporated herein by reference.

By known means as described herein, polyclonal or monoclonal antibodies, antibody fragments and binding domains and CDRs (including engineered forms of any of the foregoing), may be created that are specific to Olfml-3 protein, one or more of its respective epitopes, or conjugates of any of the foregoing, whether such antigens or epitopes are isolated from natural sources or are synthetic derivatives or variants of the natural compounds.

Antibodies may be produced from any animal source, including birds and mammals. Preferably, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is incorporated herein by reference. These techniques are further described in Marks (1992); Stemmer (1994); Gram et al. (1992); Barbas et al. (1994); and Schier et al. (1996).

Methods for producing polyclonal antibodies in various animal species, as well as for producing monoclonal antibodies of various types, including humanized, chimeric, and fully human, are well known in the art and highly predictable. Methods for producing these antibodies are also well known and predictable. For example, the following U.S. patents and patent applications provide enabling descriptions of such methods and are herein incorporated by reference: U.S. Patent Application Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024. All patents, patent application publications, and other publications cited herein and therein are hereby incorporated by reference in the present application.

It is fully expected that antibodies to Olfml-3 will have the ability to neutralize or counteract the effects of Olfml-3 regardless of the animal species, monoclonal cell line or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into antibody fragments having the binding domain or CDR. Removal of the Fc portion reduces the likelihood that the antibody fragment will elicit an undesirable immunological response and, thus, antibodies without Fc may be preferential for prophylactic or therapeutic treatments. As described above, antibodies may also be constructed so as to be chimeric, partially or fully human, so as to reduce or eliminate the adverse immunological consequences resulting from administering to an animal an antibody that has been produced in, or has sequences from, other species.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that bacteria containing such a variant may be implemented in compositions and methods. Consequently, a protein need not be isolated.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% may be an antibody that binds Olfml-3.

An antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

Embodiments provide antibodies and antibody-like molecules against Olfml-3, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules that have been attached to antibodies include toxins, therapeutic enzymes, antibiotics, radio-labeled nucleotides and the like. By contrast, a reporter molecule is defined as any moiety that may be detected using an assay. Non-limiting examples of reporter molecules that have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Several methods are known in the art for the attachment or conjugation of an antibody to its conjugate moiety. Some attachment methods involve the use of a metal chelate complex employing, for example, an organic chelating agent such as a diethylenetriaminepentaacetic acid anhydride (DTPA); ethylenetriaminetetraacetic acid; N-chloro-p-toluenesulfonamide; and/or tetrachloro-3-6α-diphenylglycouril-3 attached to the antibody. Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

III. TREATMENT OF DISEASES

Certain aspects of the present embodiments can be used to prevent or treat a disease or disorder associated with Olfml-3-mediated angiogenesis. Functioning of Olfml-3 may be reduced by any suitable substances to prevent angiogenesis. Such exemplary substances can be monoclonal anti-Olfml-3 antibodies.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an antibody that inhibits the function Olfml-3 for the purpose of minimizing the growth or invasion of a tumor, such as a colorectal cancer.

A "subject" refers to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

Certain aspects of the present invention may be used to treat any condition or disease associated with increased expression of an Olfml-3. For example, the disease may be an angiogenesis-related condition or disease. Angiogenesis-related condition or disease is a consequence of an imbalanced angiogenic process resulting in an excessive amount of new blood vessels.

In certain embodiments, the present methods can be used to inhibit angiogenesis that is non-pathogenic, i.e., angiogenesis that results from normal processes in the subject. Examples of non-pathogenic angiogenesis include endometrial neovascularization, and processes involved in the production of fatty tissues or cholesterol. Thus, the invention provides a method for inhibiting non-pathogenic angiogenesis, e.g., for controlling weight or promoting fat loss, for reducing cholesterol levels, or as an abortifacient.

The present methods can also inhibit angiogenesis that is associated with an angiogenic disease, i.e., a disease in which pathogenicity is associated with inappropriate or uncontrolled angiogenesis. For example, most cancerous solid tumors generate an adequate blood supply for themselves by inducing angiogenesis in and around the tumor site. This tumor-induced angiogenesis is often required for tumor growth, and also allows metastatic cells to enter the bloodstream.

Other angiogenic diseases include diabetic retinopathy, age-related macular degeneration (ARMD), psoriasis, rheumatoid arthritis and other inflammatory diseases. These diseases are characterized by the destruction of normal tissue by newly formed blood vessels in the area of neovascularization. For example, in ARMD, the choroid is invaded and destroyed by capillaries. The angiogenesis-driven destruction of the choroid in ARMD eventually leads to partial or full blindness. The angiogenesis-related conditions also include ocular neovascularization, arterio-venous malformations, coronary restenosis, peripheral vessel restenosis, glomerulonephritis, rheumatoid arthritis, ischemic cardiovascular pathologies, or chronic inflammatory diseases.

Exemplary eye angiogenic diseases to be treated or prevented also include choroidal neovascularization (CNV) due to any cause including but not limited to age-related macular degeneration, ocular histoplasmosis, pathologic myopia, and angioid streaks. It also applies to retinal neovascularization of any cause including but not limited to proliferative diabetic retinopathy, retinal vein occlusions, and retinopathy of prematurity. It also applies to iris neovascularization and corneal neovascularization of any causes.

The neovascularization may also be neovascularization associated with an ocular wound. For example, the wound may be the result of a traumatic injury to the globe, such as a corneal laceration. Alternatively, the wound may be the result of ophthalmic surgery. In some embodiments, the methods of the present invention may be applied to prevent or reduce the risk of proliferative vitreoretinopathy following vitreoretinal surgery, prevent corneal haze following corneal surgery (such as corneal transplantation and laser surgery), prevent closure of a trabeculectomy, prevent or substantially slow the recurrence of pterygii, and so forth.

The neovascularization may be located either on or within the eye of the subject. For example, the neovascularization may be corneal neovascularization (either located on the corneal epithelium or on the endothelial surface of the cornea), iris neovascularization, neovascularization within the vitreous cavity, retinal neovaculization, or choroidal neovascularization. The neovascularization may also be neovascularization associated with conjunctival disease.

An antibody that binds to Olfml-3 may be administered to treat a cancer. The cancer may be a solid tumor, metastatic cancer, or non-metastatic cancer. In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, prostate, skin, stomach, testis, tongue, or uterus.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

IV. PHARMACEUTICAL PREPARATIONS

Where clinical application of a composition containing a monoclonal antibody is undertaken, it will generally be beneficial to prepare a pharmaceutical composition appropriate for the intended application. This will typically entail preparing a pharmaceutical composition that is essentially free of pyrogens, as well as any other impurities that could be harmful to humans or animals. One may also employ appropriate buffers to render the complex stable and allow for uptake by target cells.

The phrases "pharmaceutical or pharmacologically acceptable" refers to molecular entities and compositions that do not produce an adverse, allergic or other untoward reaction when administered to an animal, such as a human, as appropriate. The preparation of a pharmaceutical composition comprising a inhibitory nucleic acid or additional active ingredient will be known to those of skill in the art in light of the present disclosure, as exemplified by Remington (2005), incorporated herein by reference. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. A pharmaceutically acceptable carrier is particularly formulated for administration to a human, although in certain embodiments it may be desirable to use a pharmaceutically acceptable carrier that is formulated for administration to a non-human animal but that would not be acceptable (e.g., due to governmental regulations) for administration to a human. Except insofar as any conventional carrier is incompatible with the active ingredient, its use in the therapeutic or pharmaceutical compositions is contemplated.

The actual dosage amount of a composition of the present invention administered to a patient or subject can be determined by physical and physiological factors, such as body weight, severity of condition, the type of disease being treated, previous or concurrent therapeutic interventions, idiopathy of the patient, and the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 microgram/kg/body weight to about 500 milligram/kg/body weight, etc., can be administered. Each dose may be in a volume of 1, 10, 50, 100, 200, 500, 1000 or more µl or ml or any number in between the foregoing.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters, such as ethyloleate. Aqueous carriers include water, alcoholic/aqueous solutions, saline solutions, parenteral vehicles, such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

In particular embodiments, the compositions of the present invention are suitable for application to mammalian eyes. For example, the formulation may be a solution, a suspension, or a gel. In some embodiments, the composition is administered via a biodegradable implant, such as an intravitreal implant or an ocular insert, such as an ocular insert designed for placement against a conjunctival surface. In some embodiments, the therapeutic agent coats a medical device or implantable device.

In preferred aspects the formulation of the invention will be applied to the eye in aqueous solution in the form of drops. These drops may be delivered from a single dose ampoule, which may preferably be sterile and thus render bacteriostatic components of the formulation unnecessary. Alternatively, the drops may be delivered from a multi-dose bottle, which may preferably comprise a device that extracts preservative from the formulation as it is delivered, such devices being known in the art.

In other aspects, components of the invention may be delivered to the eye as a concentrated gel or similar vehicle that forms dissolvable inserts that are placed beneath the eyelids.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration may be particularly advantageous for the treatment of skin cancers, to prevent chemotherapy-induced alopecia or other dermal hyperproliferative disorder. Alternatively, administration may be by orthotopic, intradermal, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, or respiratory tract, aerosol delivery can be used. Volume of the aerosol is between about 0.01 ml and 0.5 ml.

An effective amount of the therapeutic composition is determined based on the intended goal. For example, one skilled in the art can readily determine an effective amount of an antibody of the invention to be administered to a given subject, by taking into account factors such as the size and weight of the subject; the extent of the neovascularization or disease penetration; the age, health and sex of the subject; the route of administration; and whether the administration is regional or systemic. The term "unit dose" or "dosage" refers to physically discrete units suitable for use in a subject, each unit containing a predetermined-quantity of the therapeutic composition calculated to produce the desired responses discussed above in association with its administration, i.e., the appropriate route and treatment regimen. The quantity to be administered, both according to number of treatments and unit dose, depends on the protection or effect desired.

Precise amounts of the therapeutic composition also depend on the judgment of the practitioner and are particular to each individual. Factors affecting the dose include the physical and clinical state of the patient, the route of administration, the intended goal of treatment (e.g., alleviation of symptoms versus cure) and the potency, stability and toxicity of the particular therapeutic substance.

V. COMBINATION TREATMENTS

In certain embodiments, the compositions and methods of the present invention involve an antibody or an antibody fragment against Olfml-3 to inhibit its activity in angiogenesis, in combination with a second or additional therapy. Such therapy can be applied in the treatment of any disease that is associated with increased expression or activity of Olfml-3. For example, the disease may be an angiogenesis-related disease.

The methods and compositions including combination therapies enhance the therapeutic or protective effect, and/or increase the therapeutic effect of another anti-angiogenesis, anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an antibody and a second therapy. A tissue, tumor, or cell can be contacted with one or more compositions or pharmacological formulation(s) including one or more of the agents (i.e., an antibody or an anti-cancer agent), or by contacting the tissue, tumor, and/or cell with two or more distinct compositions or formulations, wherein one composition provides 1) an inhibitory antibody; 2) an anti-cancer agent, or 3) both an inhibitory antibody and an anti-cancer agent. Also, it is contemplated that such a combination therapy can be used in conjunction with a chemotherapy, radiotherapy, surgical therapy, or immunotherapy.

The terms "contacted" and "exposed," when applied to a cell, are used herein to describe the process by which a therapeutic antibody and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

An inhibitory antibody may be administered before, during, after or in various combinations relative to an anti-cancer treatment. The administrations may be in intervals ranging from concurrently to minutes to days to weeks. In embodiments where the inhibitor of gene expression is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the antibody and the anti-cancer therapy within about 12 to 24 or 72 h of each other and, more particularly, within about 6-12 h of each other. In some situations it may be desirable to extend the time period for treatment significantly where several days (2, 3, 4, 5, 6 or 7) to several weeks (1, 2, 3, 4, 5, 6, 7 or 8) lapse between respective administrations.

In certain embodiments, a course of treatment will last 1-90 days, or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an inhibitory antibody therapy is "A" and an anti-cancer therapy is "B":

A/B/AB/A/BB/B/AA/A/BA/B/BB/A/AA/B/B/BB/A/B/B
B/B/B/A B/B/A/B A/A/B/B A/B/A/BA/B/B/AB/B/A/A
B/A/B/A B/A/A/B A/A/A/BB/A/A/AA/B/A/AA/A/B/A

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy.

In specific aspects, it is contemplated that a standard therapy will include antiangiogenic therapy, chemotherapy, radiotherapy, immunotherapy, surgical therapy or gene therapy and may be employed in combination with the inhibitory antibody, anti-cancer therapy, or both the inhibitory antibody and the anti-cancer therapy, as described herein.

A. Antiangiogenic Therapy

The skilled artisan will understand that additional antiangiogenic therapies may be used in combination or in conjunction with methods of the invention. For example additional antiangiogenic therapies may antagonize the VEGF and/or FGF signaling pathway. Thus, in some cases and additional therapy may comprise administration an antibody that binds to VEGF, a VEGF receptor, FGF, or an FGF receptor. In certain specific aspects, methods and compositions of the invention may be used in conjunction with AVASTIN® (bevacizumab), LUCENTIS® (ranibizumab), MACUGEN® (pegaptanib sodium) or an anti-inflammatory drug. Thus, in certain specific cases there is provided a therapeutic composition comprising an anti-Olfml-3 composition and bevacizumab or pegaptanib sodium in a pharmaceutically acceptable carrier.

In still further aspects a gene that regulates angiogenesis may be delivered in conjunction with the methods of the invention. For example, in some aspects, a gene that regulates angiogenesis may be a tissue inhibitor of metalloproteinase, endostatin, angiostatin, endostatin XVIII, endostatin XV, kringle 1-5, PEX, the C-terminal hemopexin domain of matrix metalloproteinase-2, the kringle 5 domain of human plasminogen, a fusion protein of endostatin and angiostatin, a fusion protein of endostatin and the kringle 5 domain of human plasminogen, the monokine-induced by interferon-gamma (Mig), the interferon-alpha inducible protein 10 (IP10), a fusion protein of Mig and IP10, soluble FLT-1 (fms-like tyrosine kinase 1 receptor), and kinase insert domain receptor (KDR) gene. In certain specific aspects, such an angiogenic regulator gene may be delivered in a viral vector such as the lentiviral vectors described in U.S. Pat. No. 7,122,181, incorporated herein by reference.

B. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1l; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK-polysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromefihylornithine (DMFO); retinoids such as retinoic acid; capecitabine; carboplatin, procarbazine, plicomycin, gemcitabien, navelbine, farnesyl-protein tansferase inhibitors, transplatinum, and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor and a HER2 expression inhibitor; vaccines such as gene therapy vaccines and pharmaceutically acceptable salts, acids or derivatives of any of the above.

C. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287) and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

D. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

Another immunotherapy could also be used as part of a combined therapy with gene silencing therapy discussed above. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including cytokines, such as IL-2, IL-4, IL-12, GM-CSF, and gamma-IFN, chemokines, such as MIP-1, MCP-1, and IL-8, and growth factors, such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds can be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739,169; Hui and Hashimoto, 1998; Christodoulides et al., 1998), cytokine therapy, e.g., interferons α, β and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines, such as IL-2, or transduced with genes for tumor necrosis, and re-administered (Rosenberg et al., 1988; 1989).

E. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that certain aspects of the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other Agents

It is contemplated that other agents may be used in combination with certain aspects of the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increase of intercellular signaling by elevating the number of GAP junctions would increase the anti-hyperproliferative effects on the neighboring hyperproliferative cell population. In other embodiments, cytostatic or differentiation agents can be used in combination with certain aspects of the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present invention to improve the treatment efficacy.

Hormonal therapy may also be used in conjunction with certain aspects of the present invention or in combination with any other cancer therapy previously described. The use of hormones may be employed in the treatment of certain cancers such as breast, prostate, ovarian, or cervical cancer to lower the level or block the effects of certain hormones, such as testosterone or estrogen. This treatment is often used in combination with at least one other cancer therapy as a treatment option or to reduce the risk of metastases.

VI. KITS AND DIAGNOSTICS

In various aspects of the invention, a kit is envisioned containing therapeutic agents and/or other therapeutic and delivery agents. In some embodiments, the present invention contemplates a kit for preparing and/or administering a therapy of the invention. The kit may comprise one or more sealed vials containing any of the pharmaceutical compositions of the present invention. The kit may include, for example, at least one Olfml-3 antibody, as well as reagents to prepare, formulate, and/or administer the components of the invention or perform one or more steps of the inventive methods. In some embodiments, the kit may also comprise a suitable container means, which is a container that will not react with components of the kit, such as an eppendorf tube, an assay plate, a syringe, a bottle, or a tube. The container may be made from sterilizable materials, such as plastic or glass.

The kit may further include an instruction sheet that outlines the procedural steps of the methods set forth herein, and will follow substantially the same procedures as described herein or are known to those of ordinary skill. The instruction information may be in a computer readable media containing machine-readable instructions that, when executed using a computer, cause the display of a real or virtual procedure of delivering a pharmaceutically effective amount of a therapeutic agent.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Production of Monoclonal Antibodies

The inventors produced a panel of monoclonal antibodies against a recombinant Olfml-3 protein. Three antibodies against human Olfml3 were generated using standard techniques by injecting simultaneously two 14-aa long peptides comprising epitopes in the coiled-coil (peptide A, 86-99 aa: RVDRLEREVDYLET; SEQ ID NO: 5) and the olfactomedin-like domains (peptide B, 390-403 aa: GYQIVYKLEMRKKE; SEQ ID NO: 6) as immunogens in rats (Aurrand-Lions et al., 1996). Briefly, human Olfml3 peptides A and B coupled to 100 μg KLH carrier protein (keyhole limpet hemocyanin, Pierce) and mixed with adjuvant 56322 (Sigma), were used to immunize female Wister rats. In total, three injections were performed every 9 days. Two days after a final s.c. injection of human Olfml3 peptides, blasts from draining lymph nodes were fused to Sp2/0 cells, and hybridomas were selected in HAT-containing medium (Life Technologies). Growing clones were screened by ELISA for the production of monoclonal antibodies recognizing specifically human Olfml3-FLAG. Positive clones were subcloned, rescreened, and further tested. Antibodies were purified on protein G-Sepharose columns (GE HealthCare) according to the manufacturer instructions. Two Olfml3-binding antibodies, 46A9BO and 9F8BO, are of IgG2b isotype subclass and one, Z14A7, is of IgG2c isotype subclass. The 46A9BO and 9F8BO monoclonal antibodies were used for in vivo tumor graft models.

The VH and VL chains of antibodies 46A9BO, 9F8BO and Z14A7 were sequenced and the complementarity determining regions (CDRs) determined. Total RNA was extracted from the hybridoma cell pellets and cDNA was created from the RNA by reverse-transcription with an oligo(dT) primer. PCR reactions using variable domain primers to amplify both the VH and VL regions of the monoclonal antibody DNA were performed. The products were extracted and gel purified and then cloned into the Invitrogen sequencing vector pCR2.1 and transformed into TOP10 for positive transformants. Selected colonies were picked and analyzed through sequencing, from which a consensus sequence for each antibody was generated (Table 1). The CDRs were determined by the IMGT numbering system (Lefranc et al., 1999).

Antibody 46A9BO comprises VH CDR sequences corresponding to SEQ ID NOs: 7, 8, and 9 and VL CDR sequences corresponding to SEQ ID NOs: 10, 11, and 12. Antibody 9F8BO comprises VH CDR sequences corresponding to SEQ ID NOs: 21, 22, and 23 and VL CDR sequences corresponding to SEQ ID NOs: 24, 25, and 26. Antibody Z14A7 comprises VH CDR sequences corresponding to SEQ ID NOs: 13, 14, and 15 and VL CDR sequences corresponding to SEQ ID NOs: 16, 5, and 6.

Figure 5:
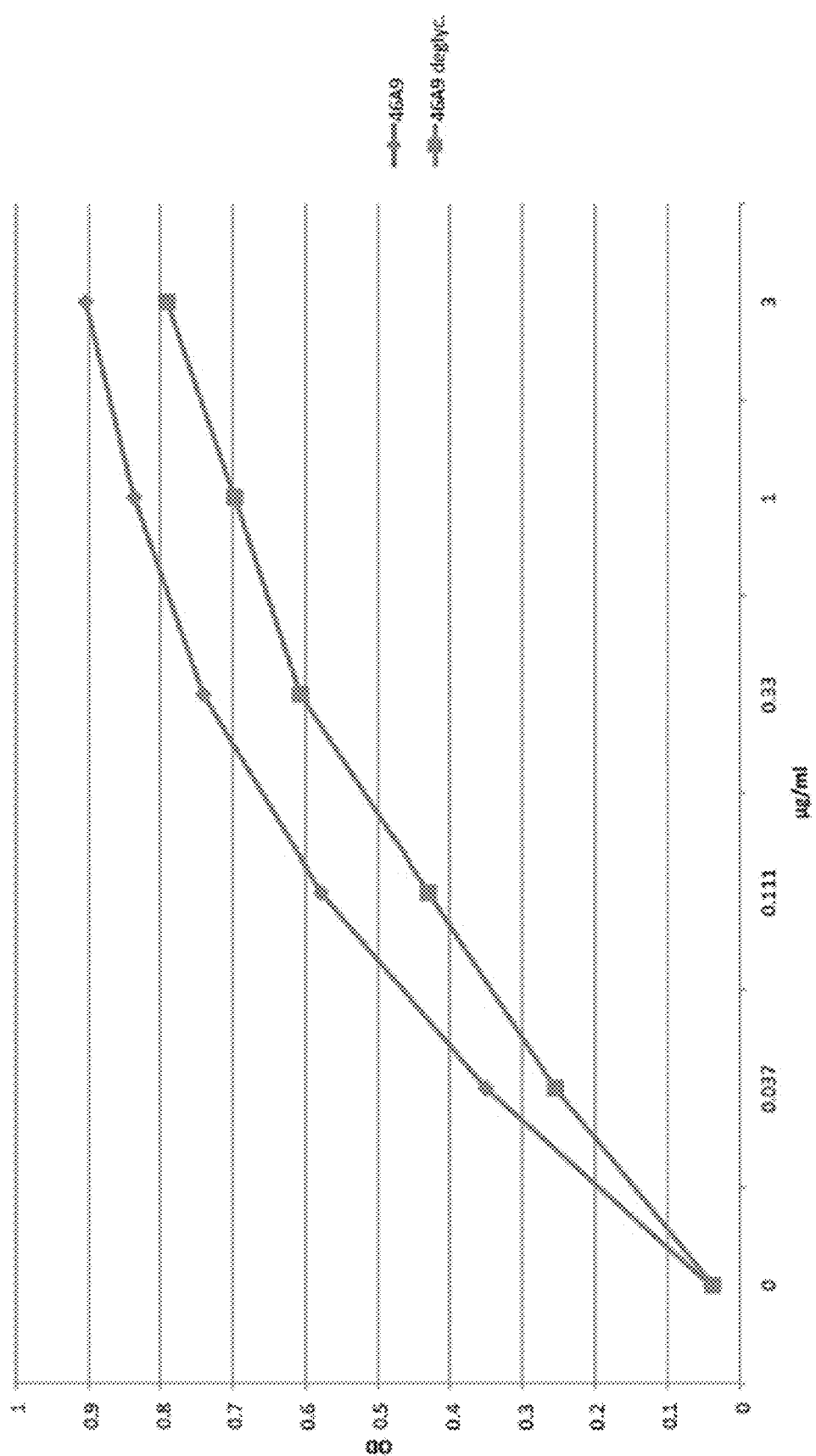
FIG. 5. Graph shows ELISA studies of 46A9BO antibody binding to recombinant soluble Olfml-3 protein. Studies were conducted with both glycosylated and deglycosylated 46A9BO antibodies and results showed that antigen recognition was largely independent of antibody glycosylation.

Additional studies with the 46A9BO antibodies showed that antigen recognition was largely independent of antibody glycosylation. ELISA studies showed that recombinant soluble Olfml-3 protein bound to 46A9BO antibody in a dose dependent fashion regardless of whether the antibody had been deglycosylated (see, FIG. 5), though glycosylated antibody bound antigen more effectively. The same results were achieved when testing the binding of glycosylated and deglycosylated 46A9BO to the Olfml-3 peptide B sequence (in both cases no binding to the peptide A sequences was observed).

Example 2—Anti-Olfml-3 Monoclonal Antibodies 46A9BO and 9F8BO Reduce Tumor Growth In Vivo Eight- to 10-week-old female C56BL6/J mice were inoculated subcutaneously (s.c.) with $0.5 \times 10^6$ murine Lewis lung carcinoma cells (LLC1; obtained from the European Collection of Cell Cultures, Salisbury, United Kingdom). Mice were then injected i.p. with the antibodies as follows: at day 1: 50 μg, at day 5: 50 μg and at day 8: 50 μg of monoclonal antibody 46A9BO, monoclonal antibody 9F8BO or isotype-matched control rat IgG2B antibody. Tumors were excised and analyzed on the ninth day. Tumor weight was measured.

The tumor weights were significantly decreased in mice treated with either 46A9BO or 9F8BO anti-Olfml-3 antibodies compared to the isotype-matched control antibody (FIG. 1). Since LLC1 tumors do not express Olfml-3, the reduction in tumor growth was due to an effect of the anti-Olfml-3 antibodies on tumor angiogenesis.

Figure 2:
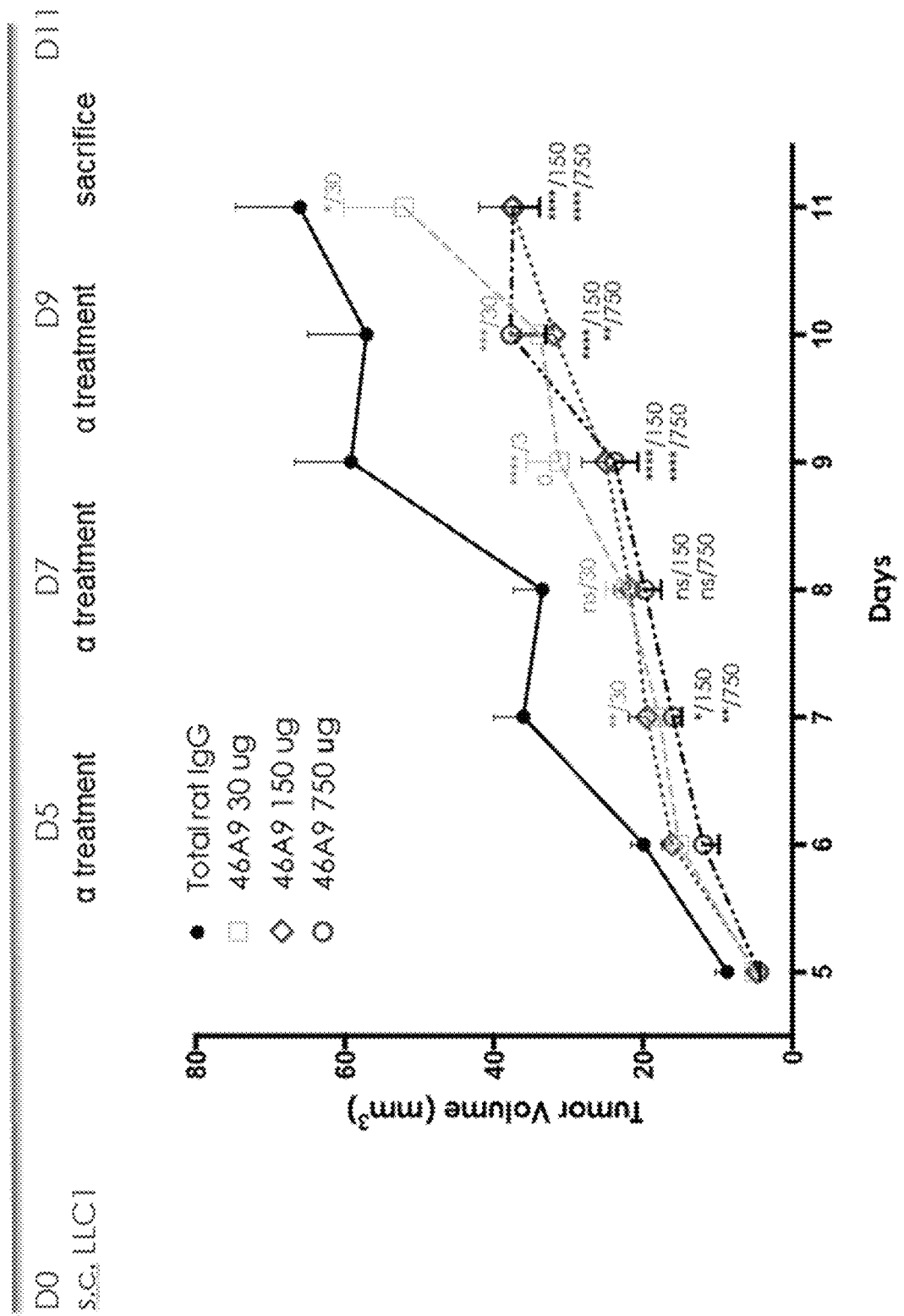
FIG. 2. Graph shows the results of further studies to assess the inhibitory effects of 46A9 monoclonal antibodies against human Olfml3 on tumor growth. Mice were inoculated subcutaneously (s.c.) with LLC1 cells and subsequently injected with control rat IgG or 30, 150 or 750 µg of 46A9 on days 5, 7 and 9 after inoculation. On day 11 the animals were sacrificed. Tumor volumes were measured throughout the course of the study and the results are graphed.

In order to test the therapeutic and dose effect, further studies were undertaken to assess the in vivo tumor growth inhibiting activity of the 46A9 antibody. Again, mice were inoculated s.c. with LLC1 cells. The inoculated mice were then treated with control rat IgG or 30, 150 or 750 μg of 46A9 on days 5, 7 and 9 after inoculation. On day 11 the animals were sacrificed. Tumor volumes were measured throughout the course of the studies. The results are shown in the graph of FIG. 2, which demonstrates that all tested doses of the 46A9 antibody achieved statistically significant reductions in tumor volume.

Following sacrifice of mice on day 11 tissue samples were collected and subjected to histological analysis to assess any potential toxicity. Detailed analysis of lung, heart, liver and kidney tissue samples from the mice revealed no signs of toxicity even at the maximal tested dosage of 750 μg of 46A9. Accordingly, the anti-Olfml-3 therapy appears to be essentially non-toxic under the tested conditions.

Figure 3:
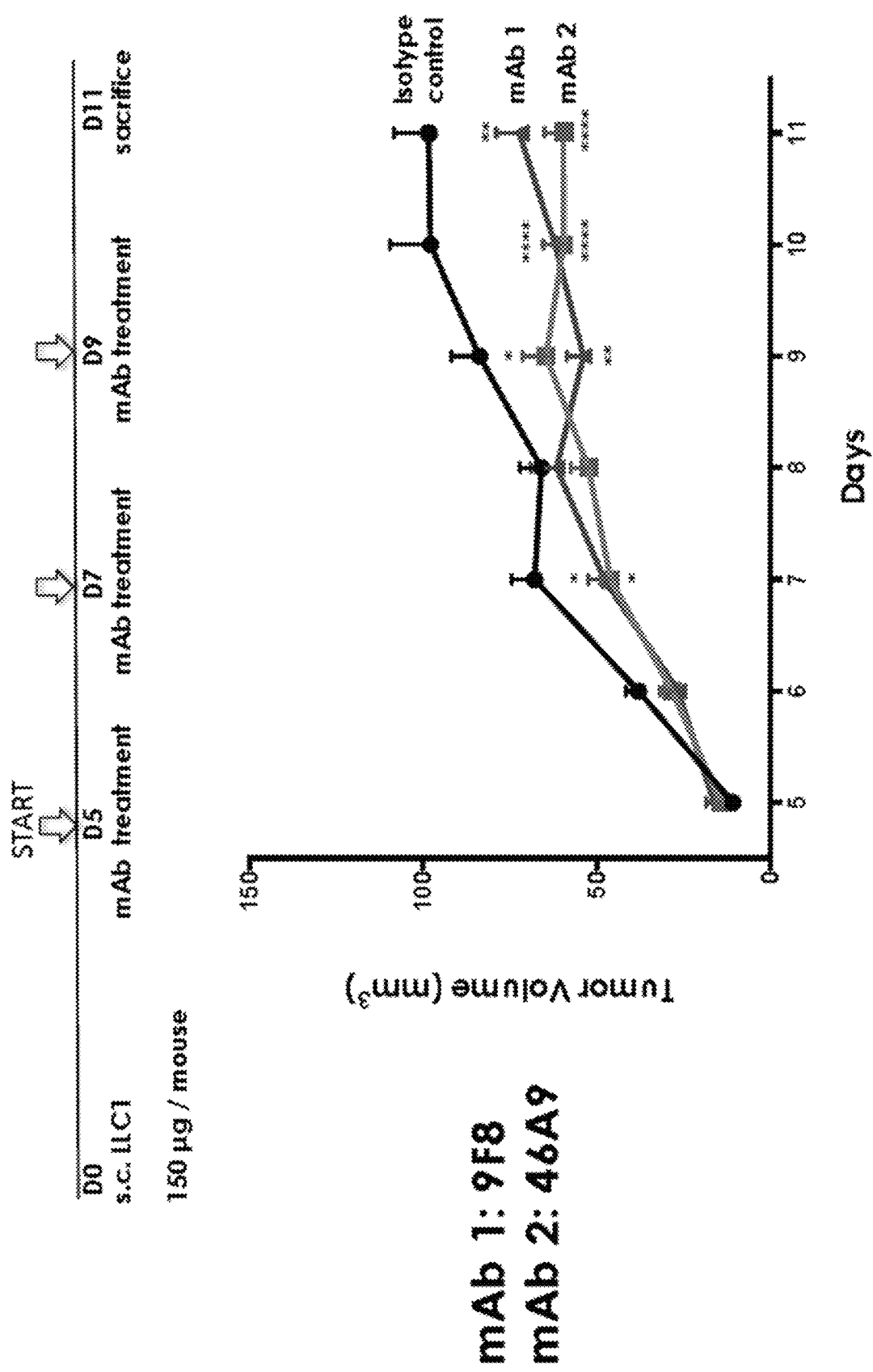
FIG. 3. Graph shows the results of further studies to assess the inhibitory effects of the 9F8 (mAb 1) and 46A9 (mAb 2) monoclonal antibodies against human Olfml3 on tumor growth. Mice were inoculated s.c. with LLC1 cells and subsequently injected with control rat IgG, 9F8 or 46A9 antibodies (in a dose of 150 µg per mouse) on days 5, 7 and 9 after inoculation. On day 11, the animals were sacrificed. Tumor volumes were measured throughout the course of the study and the results were graphed. Error bars are marked as follows: *p<0.05; p<0.01; *p<0.001; and ****p<0.0001.

Additional murine studies were undertaken to assess the potential anti-tumor activity of the 9F8 (mAb 1) and 46A9 (mAb 2) monoclonal antibodies. The studies were essentially completed as detailed above. Briefly, mice were inoculated subcutaneously with LLC1 cells and subsequently injected with control rat IgG, 9F8 or 46A9 antibodies (in a dose of 150 μg per mouse) on days 5, 7 and 9 after inoculation. On day 11, the animals were sacrificed. Tumor volumes were measured throughout the course of the study and the results were graphed. As shown in the graph of FIG. 3, the studies demonstrate that both the 9F8 and 46A9 antibodies were able to significantly inhibit tumor growth relative to control antibody treatment.

Figure 4A:
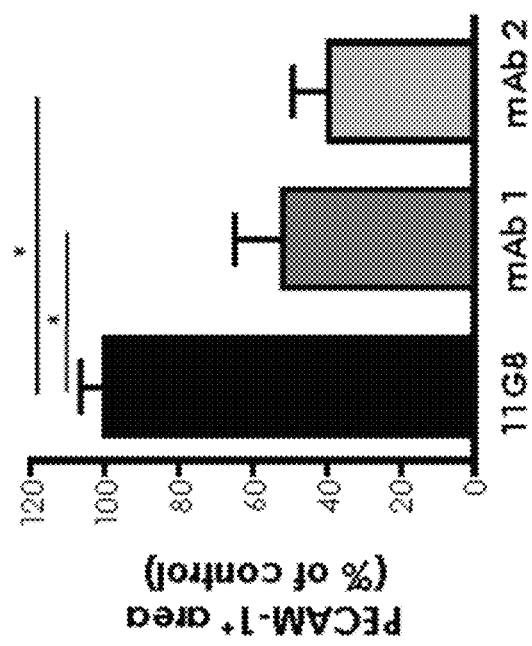
FIG. 4A-B. A, Graph shows the results of immunofluorescence studies in tumor tissues exposed the 9F8 (mAb 1) or 46A9 (mAb 2) monoclonal antibodies or to control (11G8) antibodies. Tumor tissue sections were stained with DAPI and immunofluorescently labeled to detect PECAM-1, as a marker of vascularization. The proportion of PECAM-1 positive tissue area was quantitated (as a percentage of the area detected in the control treated sample) and the results were graphed. B, Further immunofluorescence studies were used to determine the amount of pericyte coverage in treated tumor tissues. Again, tissues exposed to the 9F8 (mAb 1) or 46A9 (mAb 2) monoclonal antibodies or to control (11G8) antibodies were sectioned. Tumor tissue sections were stained with DAPI and immunofluorescently labeled to detect PECAM-1 and α-SMA, to determine pericyte coverage in the tissues. The proportion α-SMA$^+$ area and α-SMA$^+$ pericyte coverage in the tissues were quantitated and graphed.
Figure 4B:
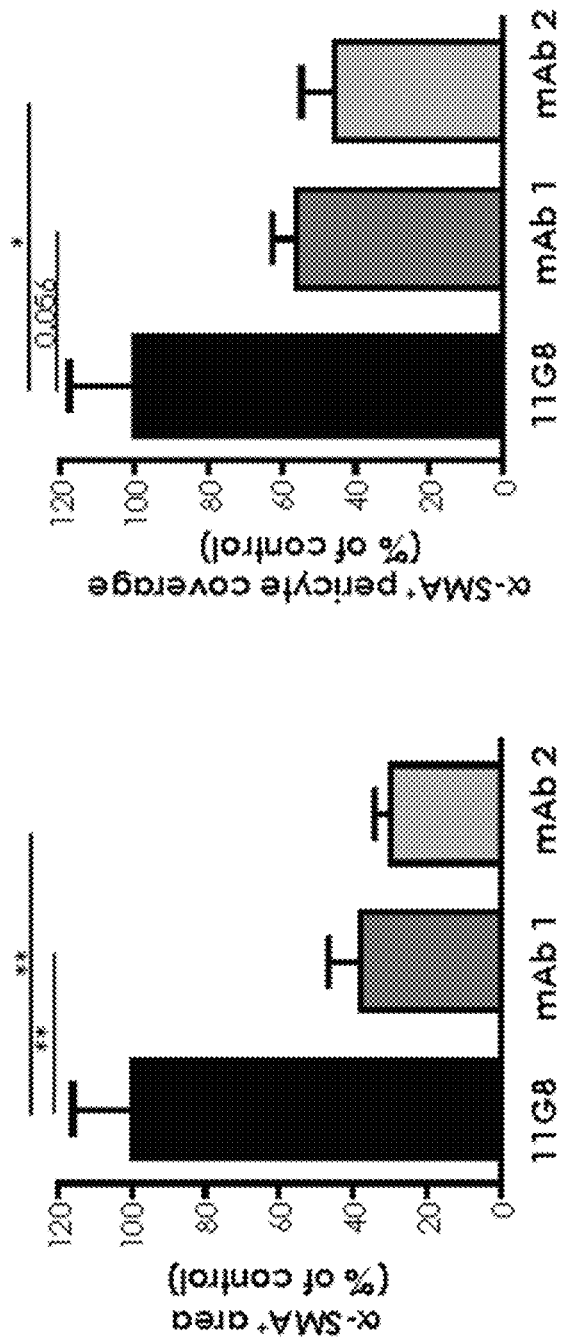

Further studies were completed to assess the effect of the 9F8 and 46A9 antibodies on tumor vascularization. For these studies, tissue sections were harvested from tumors exposed to 9F8, 46A9 or a control antibody. Tissue sections were labeled to detect PECAM-1 as a marker of vascularization. The proportion of PECAM positive tissue area was quantitated and the results are presented in the graph of FIG. 4A. Similarly, tumor tissue sections were stained with DAPI and immunofluorescently labeled to detect PECAM-1 and α-SMA, to determine pericyte coverage in treated tumor tissues. The proportion α-SMA$^+$ area and α-SMA$^+$ pericyte coverage in the tissues were graphed and are shown in FIG. 4B. Thus, these studies demonstrate that both studied anti-Olfml-3 antibodies were able to significantly reduce tumor tissue vascularization as measured by PECAM-1 expression and pericyte coverage.

TABLE 1

Antibody sequences.

| mAb | Heavy Chain Sequence | | | Light Chain Sequence | | |
|---|---|---|---|---|---|---|
| | CDR1 | CDR2 | CDR3 | CDR1 | CDR2 | CDR3 |
| | Amino acid sequence | | | Amino acid sequence | | |
| IgG2b | | | | | | |
| 46A9BO | GFTFSNAA (SEQ ID NO: 7) AVHLVESGGGLVQPKESLKISCAAS<u>GF TFSNAA</u>MYWVRQAPGKGLEWVAR<u>IRTK PNDY</u>ATYYVDSVKGRFTISRDDSQSMV YLQMDNLKTEDTAMYYC<u>TAFTEPDY</u>WG QGVMVTVSS (SEQ ID NO: 1) | IRTKPNDY AT (SEQ ID NO: 8) | TAFTEPDY (SEQ ID NO: 9) | ELSKTY (SEQ ID NO: 10) LIQPPSASVTLGSTVSLTCVGD<u>ELSKT YAHW</u>YQQKPDKTIVSVIY<u>KDS</u>ERPSGI SDRFSGSSSGTTATLTIHGTLAEDEAD YYC<u>LSTYSDDNLPV</u>FGGGTKLTVL (SEQ ID NO: 2) | KDS (SEQ ID NO: 11) | LSTYSDDN LPV (SEQ ID NO: 12) |
| 9F8BO | GFSLTRNN (SEQ ID NO: 21) QVQLKESGPGLVQPSQTLSLTCTVS<u>GF SLTRNN</u>VHWVRQPPGKGLEWMG<u>RMRYN GDT</u>SYNSALKSRLSISRDTSKNQVFLK MNSLQIDDTGTYYC<u>SREGYYDGTYYPD YW</u>GQGVMVTVSS (SEQ ID NO: 19) | MRYNGDT (SEQ ID NO: 22) | SREGYYDG TYYPDY (SEQ ID NO: 23) | SGDELSNKY (SEQ ID NO: 24) SVTSYELIQPPSASVTLENTVSITC<u>SG DELSNKY</u>AHWYQQKPDKTILEVMY<u>KDS</u> ERPSGISDRFSGSSSGTTAILTIRDAQ AEDEADYYC<u>LSTYSDDDLPV</u>FGGGTKL TVL (SEQ ID NO: 20) | KDS (SEQ ID NO: 25) | LSTYSDDD LPV (SEQ ID NO: 26) |

TABLE 1-continued

Antibody sequences.

| mAb | Heavy Chain Sequence | | | Light Chain Sequence | | |
|---|---|---|---|---|---|---|
| | CDR1 | CDR2 | CDR3 | CDR1 | CDR2 | CDR3 |
| | Amino acid sequence | | | Amino acid sequence | | |
| IgG2c | | | | | | |
| Z14A7 | GFTFSNAW (SEQ ID NO: 13) | IKAKSNNY AT (SEQ ID NO: 14) | LYGYYFDY (SEQ ID NO: 15) | QSLIHSNG NTY (SEQ ID NO: 16) | RIS (SEQ ID NO: 17) | LQGTHLPFT (SEQ ID NO: 18) |
| | EVQLVETGGSLVQPGKSLKLTCATSGF TFSNAWMHWVRQSPEKQLEWVAQIKAK SNNYATYYAESVKGRFTISRDDSKSSI YLQMNSLKEEDTAIYYCLYGYYFDYWG QGVMVTVSS (SEQ ID NO: 3) | | | DVVMTQTPVSLPVSLGGQASISCRSSQ SLIHSNGNTYLHWFLQKPGQSPQLLIY RISNRFSGVPDRFSGSGSGTDFTLKIS RVESEDLGLYYCLQGTHLPFTFGSGTK LEIKR (SEQ ID NO: 4) | | |

Example 3—Toxicity Studies with the 46A9BO Anti-Olfml-3 Monoclonal Antibody

To assess the potential toxicity of anti-Olfml-3 monoclonal antibodies, mice were injected with a high dose (750 μg) of the 46A9BO or total rat IgG as a control. Following the treatments mice were sacrificed and subjected to pathological analysis. Stained organ tissues sections were subject to microscopic examination to detect any signs of toxicity. No differences in tissue architecture were found when comparing the lung, liver, heart or kidney tissue sections between 46A9BO treated animals and controls. Thus, even when administered at high dosage, the anti-Olfml-3 monoclonal antibody exhibited no detectable toxicity in a murine model system.

Example 4—Human Tissue Staining with the 9F8BO and 46A9BO Anti-Olfml-3 Monoclonal Antibodies The effectiveness of anti-Olfml-3 monoclonal antibodies for immunofluorescence (IF) staining of human tissues was further studied. Frozen human tissue sections were visualized, separately or in combination, using anti-Olfml-3 monoclonal antibodies and antibodies to VE-Cadherin. For example, IF studies of normal breast tissue versus metastatic ductal breast cancer (sample H14003743) showed significantly enhanced 9F8 labeling in tumor tissues, which largely overlapped with VE-expression. Likewise, IF studies of normal tissue versus a uterus, epithelial and smooth muscle carcinosarcoma tumor (sample H14003537) showed significantly enhanced 9F8 labeling in tumor tissues, again, largely overlapped with VE-expression. Further IF studies with the 46A9 antibodies also showed significantly increased 46A9 staining in human colon adenocarcinoma sections (sample H14002691) versus normal tissue. 46A9 in these tissues largely overlapped with VE-Cadherin staining.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,469,797
U.S. Pat. No. 4,472,509
U.S. Pat. No. 4,606,855
U.S. Pat. No. 4,703,003
U.S. Pat. No. 4,742,159
U.S. Pat. No. 4,767,720
U.S. Pat. No. 4,816,567
U.S. Pat. No. 4,867,973
U.S. Pat. No. 4,870,287
U.S. Pat. No. 4,938,948
U.S. Pat. No. 4,946,778
U.S. Pat. No. 5,021,236
U.S. Pat. No. 5,091,513
U.S. Pat. No. 5,164,296
U.S. Pat. No. 5,196,066
U.S. Pat. No. 5,223,409
U.S. Pat. No. 5,403,484
U.S. Pat. No. 5,420,253
U.S. Pat. No. 5,565,332
U.S. Pat. No. 5,571,698
U.S. Pat. No. 5,627,052
U.S. Pat. No. 5,656,434
U.S. Pat. No. 5,739,169
U.S. Pat. No. 5,760,395
U.S. Pat. No. 5,770,376
U.S. Pat. No. 5,789,208

U.S. Pat. No. 5,801,005
U.S. Pat. No. 5,821,337
U.S. Pat. No. 5,824,311
U.S. Pat. No. 5,830,880
U.S. Pat. No. 5,844,091
U.S. Pat. No. 5,846,945
U.S. Pat. No. 5,858,657
U.S. Pat. No. 5,861,155
U.S. Pat. No. 5,871,907
U.S. Pat. No. 5,969,108
U.S. Pat. No. 6,054,297
U.S. Pat. No. 6,165,464
U.S. Pat. No. 6,365,157
U.S. Pat. No. 6,406,867
U.S. Pat. No. 6,709,659
U.S. Pat. No. 6,709,873
U.S. Pat. No. 6,753,407
U.S. Pat. No. 6,814,965
U.S. Pat. No. 6,849,259
U.S. Pat. No. 6,861,572
U.S. Pat. No. 6,875,434
U.S. Pat. No. 6,881,557
U.S. Pat. No. 6,891,024
U.S. Pat. No. 6,946,546
U.S. Patent Publn. 2002/0172677
U.S. Patent Publn. 2004/0126828
U.S. Patent Publn. 2005/0214860
Ahmed et al., *Invest. Ophthalmol. Vis. Sci.*, 45:3081-3090, 2004.
Aurrand-Lions et al., *Immunity*, 5, 391-405, 1996.
Austin-Ward and Villaseca, *Revista Medica de Chile*, 126 (7):838-845, 1998.
Barbas et al., *Proc. Natl. Acad. Sci., USA*, 91:3809-3813, 1994.
Barembaum et al., *Nat. Cell Biol.*, 2:219-225, 2000.
Bukowski et al., *Clinical Cancer Res.*, 4(10):2337-2347, 1998.
Carmeliet, *Nat. Med.*, 9:653-660, 2003.
Carmeliet, *Nature*, 438:932-936, 2005.
Christodoulides et al., *Microbiology*, 144(Pt 11): 3027-3037, 1998.
Davidson et al., *J. Immunother.*, 21(5):389-398, 1998.
Ferris et al., *Arch. Ophthalmol.*, 102(11):1640-1642, 1984.
Folkman, *N. Engl. J. Med.*, 285:1182-1186, 1971.
Folkman, *Nat. Med.*, 1:27-31, 1995.
Gariano and Gardner, *Nature*, 438:960-966, 2005.
Gram et al., *Proc. Natl. Acad. Sci. USA*, 89:3576-3580, 1992.
Hanahan, *Science*, 277:48-50, 1997.
Hanibuchi et al., *Int. J. Cancer*, 78(4):480-485, 1998.
Harland, *Cell*, 134: 718-719, 2008.
Hellstrand et al., *Acta Oncologica*, 37(4):347-353, 1998.
Hu et al., *Cancer Res.*, 56:3055-3061, 1996.
Hui and Hashimoto, *Infection Immun.*, 66(11):5329-5336, 1998.
Ikeya et al., *Int. J. Dev. Biol.*, 49:807-823, 2005.
Inomata et al., *Cell*, 134: 854-865, 2008.
Ju et al., *Gene Ther.*, 7(19):1672-1679, 2000.
Klein et al., *Arch. Ophthalmol.*, 102:520-526, 1984.
Lefranc et al., *Nuc. Acids Res.*, 27:209-212, 1999.
Li et al., *Arterioscler. Thromb. Vasc. Biol.*, 29:1200-6, 2009.
Liu et al., *Cell Mol. Biol.*, 49:209-216, 2003.
Marks et al., *Bio/Technol.*, 10:779-783, 1992.
Mitchell et al., *Ann. NY Acad. Sci.*, 690:153-166, 1993.
Mitchell et al., *J. Clin. Oncol.*, 8(5):856-869, 1990.
Moreno and Bronner-Fraser, 2005.
Morton et al., *Arch. Surg.*, 127:392-399, 1992.
Pietras et al., *Oncogene*, 17(17):2235-2249, 1998.
Qin et al., *Proc. Natl. Acad. Sci. USA*, 95(24):14411-14416, 1998.
Ravindranath and Morton, *Intern. Rev. Immunol.*, 7: 303-329, 1991.
Rosenberg et al., *Ann. Surg.*, 210(4):474-548, 1989.
Rosenberg et al., *N. Engl. J. Med.*, 319:1676, 1988.
Sakuragi et al., *Mech Dev* 123, 114-123, 2006.
Schier et al., *Gene*, 169(2):147-155, 1996.
Snyder et al., *Biochemistry*, 30:9143-9153, 1991.
Stemmer, *Nature*, 370:389-391, 1994.
Tomarev and Nakaya, *Mol. Neurobiol.*, 40: 122-138, 2009.
Tsuda et al., *Neuron.*, 33:515-528, 2002.
Yancopoulos et al., *Nature*, 407:242-248, 2000.
Yokoe and Anholt, *Proc. Natl. Acad. Sci. USA*, 90:4655-4659, 1993.
Zeng et al., *FEBS Lett.*, 571:74-80, 2004.

---

What is claimed is:

1. An isolated monoclonal antibody, wherein the antibody specifically binds to Olfml-3 and is selected from the group consisting of:
   (a) an antibody comprising a first VH CDR having the sequence of VH CDR1 of SEQ ID NO: 7, a second VH CDR having the sequence of VH CDR2 of SEQ ID NO: 8, a third VH CDR having the sequence of VH CDR3 of SEQ ID NO: 9, a first VL CDR having the sequence of VL CDR1 of SEQ ID NO: 10, a second VL CDR having the sequence of VL CDR2 of SEQ ID NO: 11, and a third VL CDR having the sequence of VL CDR3 of SEQ ID NO: 12;
   (b) an antibody comprising a first VH CDR having the sequence of VH CDR1 of SEQ ID NO: 21, a second VH CDR having the sequence of VH CDR2 of SEQ ID NO: 22, a third VH CDR having the sequence of VH CDR3 of SEQ ID NO: 23, a first VL CDR having the sequence of VL CDR1 of SEQ ID NO: 24, a second VL CDR having the sequence of VL CDR2 of SEQ ID NO: 25, and a third VL CDR having the sequence of VL CDR3 of SEQ ID NO: 26; and
   (c) an antibody comprising a first VH CDR having the sequence of VH CDR1 of SEQ ID NO: 13, a second VH CDR having the sequence of VH CDR2 of SEQ ID NO: 14, a third VH CDR having the sequence of VH CDR3 of SEQ ID NO: 15, a first VL CDR having the sequence of VL CDR1 of SEQ ID NO: 16, a second VL CDR having the sequence of VL CDR2 of SEQ ID NO: 17, and a third VL CDR having the sequence of VL CDR3 of SEQ ID NO: 18.

2. The isolated antibody of claim 1, wherein the antibody comprises:
   (a) a first VH CDR is identical to SEQ ID NO: 7;
   (b) a second VH CDR is identical to SEQ ID NO: 8;
   (c) a third VH CDR is identical to SEQ ID NO: 9;
   (d) a first VL CDR is identical to SEQ ID NO: 10;
   (e) a second VL CDR is identical to SEQ ID NO: 11; and
   (f) a third VL CDR is identical to SEQ ID NO: 12.

3. The isolated antibody of claim 1, wherein the antibody comprises:
   (a) a first VH CDR is identical to SEQ ID NO: 21;
   (b) a second VH CDR is identical to SEQ ID NO: 22;
   (c) a third VH CDR is identical to SEQ ID NO: 23;
   (d) a first VL CDR is identical to SEQ ID NO: 24;
   (e) a second VL CDR is identical to SEQ ID NO: 25; and
   (f) a third VL CDR is identical to SEQ ID NO: 26.

4. The isolated antibody of claim 1, wherein the antibody comprises:
   (a) a first VH CDR is identical to SEQ ID NO: 13;
   (b) a second VH CDR is identical to SEQ ID NO: 14;
   (c) a third VH CDR is identical to SEQ ID NO: 15;
   (d) a first VL CDR is identical to SEQ ID NO: 16;
   (e) a second VL CDR is identical to SEQ ID NO: 17; and
   (f) a third VL CDR is identical to SEQ ID NO: 18.

5. The antibody of claim 1, wherein the antibody comprises:
   (i) a VH domain identical to the VH domain of SEQ ID NO: 1 and a VL domain identical to the VL domain of SEQ ID NO: 2;
   (i) a VH domain identical to the VH domain of SEQ ID NO: 19 and a VL domain identical to the VL domain of SEQ ID NO: 20; or
   (iii) a VH domain identical to the VH domain of SEQ ID NO: 3 and a VL domain identical to the VL domain of SEQ ID NO: 4.

6. The antibody of claim 5, wherein the antibody comprises a VH domain identical to the VH domain of SEQ ID NO: 1 and a VL domain identical to the VL domain of SEQ ID NO: 2.

7. The antibody of claim 5, wherein the antibody comprises a VH domain identical to the VH domain of SEQ ID NO: 19 and a VL domain identical to the VL domain of SEQ ID NO: 20.

8. The antibody of claim 5, wherein the antibody comprises a VH domain identical to the VH domain of SEQ ID NO: 3 and a VL domain identical to the VL domain of SEQ ID NO: 4.

9. The antibody of claim 1, wherein the antibody is recombinant.

10. The antibody of claim 1, wherein the antibody is an IgG, IgM, IgA or an antigen binding fragment thereof.

11. The antibody of claim 1, wherein the antibody is a Fab', a F(ab')2, a F(ab')3, a monovalent scFv, a bivalent scFv, or a single domain antibody.

12. The antibody of claim 1, wherein the antibody is a human, humanized antibody or de-immunized antibody.

13. The antibody of claim 1, wherein the antibody is conjugated to an imaging agent, a chemotherapeutic agent, a toxin or a radionuclide.

14. A composition comprising an antibody of claim 1 in a pharmaceutically acceptable carrier.

15. A method of treating an angiogenesis-related condition in a subject comprising administering to the subject an amount of an antibody in accordance with of claim 1 that is effective to treat the angiogenesis-related condition wherein the angiogenesis-related condition comprises cancer.

* * * * *

SEQUENCE LISTING

```
<160> NUMBER OF SEQ ID NOS: 26

<210> SEQ ID NO 1
<211> LENGTH: 117
<212> TYPE: PRT
<213> ORGANISM: Artificial Sequence
<220> FEATURE:
<223> OTHER INFORMATION: monoclonal antibody fragment

<400> SEQUENCE: 1

Ala Val His Leu Val Glu Ser Gly Gly Gly Leu Val Gln Pro Lys Glu
1               5                   10                  15

Ser Leu Lys Ile Ser Cys Ala Ala Ser Gly Phe Thr Phe Ser Asn Ala
            20                  25                  30

Ala Met Tyr Trp Val Arg Gln Ala Pro Gly Lys Gly Leu Glu Trp Val
        35                  40                  45

Ala Arg Ile Arg Thr Lys Pro Asn Asp Tyr Ala Thr Tyr Tyr Val Asp
    50                  55                  60

Ser Val Lys Gly Arg Phe Thr Ile Ser Arg Asp Asp Ser Gln Ser Met
65                  70                  75                  80
```

```
Val Tyr Leu Gln Met Asp Asn Leu Lys Thr Glu Asp Thr Ala Met Tyr
                85                  90                  95

Tyr Cys Thr Ala Phe Thr Glu Pro Asp Tyr Trp Gly Gln Gly Val Met
                100                 105                 110

Val Thr Val Ser Ser
        115

<210> SEQ ID NO 2
<211> LENGTH: 105
<212> TYPE: PRT
<213> ORGANISM: Artificial Sequence
<220> FEATURE:
<223> OTHER INFORMATION: monoclonal antibody fragment

<400> SEQUENCE: 2

Leu Ile Gln Pro Pro Ser Ala Ser Val Thr Leu Gly Ser Thr Val Ser
1               5                   10                  15

Leu Thr Cys Val Gly Asp Glu Leu Ser Lys Thr Tyr Ala His Trp Tyr
                20                  25                  30

Gln Gln Lys Pro Asp Lys Thr Ile Val Ser Val Ile Tyr Lys Asp Ser
            35                  40                  45

Glu Arg Pro Ser Gly Ile Ser Asp Arg Phe Ser Gly Ser Ser Ser Gly
50                  55                  60

Thr Thr Ala Thr Leu Thr Ile His Gly Thr Leu Ala Glu Asp Glu Ala
65                  70                  75                  80

Asp Tyr Tyr Cys Leu Ser Thr Tyr Ser Asp Asp Asn Leu Pro Val Phe
                85                  90                  95

Gly Gly Gly Thr Lys Leu Thr Val Leu
                100                 105

<210> SEQ ID NO 3
<211> LENGTH: 117
<212> TYPE: PRT
<213> ORGANISM: Artificial Sequence
<220> FEATURE:
<223> OTHER INFORMATION: monoclonal antibody fragment

<400> SEQUENCE: 3

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
                20                  25                  30

Trp Met His Trp Val Arg Gln Ser Pro Glu Lys Gln Leu Glu Trp Val
            35                  40                  45

Ala Gln Ile Lys Ala Lys Ser Asn Asn Tyr Ala Thr Tyr Tyr Ala Glu
50                  55                  60

Ser Val Lys Gly Arg Phe Thr Ile Ser Arg Asp Asp Ser Lys Ser Ser
65                  70                  75                  80

Ile Tyr Leu Gln Met Asn Ser Leu Lys Glu Glu Asp Thr Ala Ile Tyr
                85                  90                  95

Tyr Cys Leu Tyr Gly Tyr Tyr Phe Asp Tyr Trp Gly Gln Gly Val Met
                100                 105                 110

Val Thr Val Ser Ser
        115

<210> SEQ ID NO 4
<211> LENGTH: 113
<212> TYPE: PRT
```

<213> ORGANISM: Artificial Sequence
<220> FEATURE:
<223> OTHER INFORMATION: monoclonal antibody fragment

<400> SEQUENCE: 4

```
Asp Val Val Met Thr Gln Thr Pro Val Ser Leu Pro Val Ser Leu Gly
1               5                   10                  15
Gly Gln Ala Ser Ile Ser Cys Arg Ser Gln Ser Leu Ile His Ser
            20                  25                  30
Asn Gly Asn Thr Tyr Leu His Trp Phe Leu Gln Lys Pro Gly Gln Ser
            35                  40                  45
Pro Gln Leu Leu Ile Tyr Arg Ile Ser Asn Arg Phe Ser Gly Val Pro
50                  55                  60
Asp Arg Phe Ser Gly Ser Gly Ser Gly Thr Asp Phe Thr Leu Lys Ile
65                  70                  75                  80
Ser Arg Val Glu Ser Glu Asp Leu Gly Leu Tyr Tyr Cys Leu Gln Gly
                85                  90                  95
Thr His Leu Pro Phe Thr Phe Gly Ser Gly Thr Lys Leu Glu Ile Lys
            100                 105                 110
Arg
```

<210> SEQ ID NO 5
<211> LENGTH: 14
<212> TYPE: PRT
<213> ORGANISM: Homo sapiens

<400> SEQUENCE: 5

```
Arg Val Asp Arg Leu Glu Arg Glu Val Asp Tyr Leu Glu Thr
1               5                   10
```

<210> SEQ ID NO 6
<211> LENGTH: 14
<212> TYPE: PRT
<213> ORGANISM: Homo sapiens

<400> SEQUENCE: 6

```
Gly Tyr Gln Ile Val Tyr Lys Leu Glu Met Arg Lys Lys Glu
1               5                   10
```

<210> SEQ ID NO 7
<211> LENGTH: 8
<212> TYPE: PRT
<213> ORGANISM: Artificial Sequence
<220> FEATURE:
<223> OTHER INFORMATION: monoclonal antibody fragment

<400> SEQUENCE: 7

```
Gly Phe Thr Phe Ser Asn Ala Ala
1               5
```

<210> SEQ ID NO 8
<211> LENGTH: 10
<212> TYPE: PRT
<213> ORGANISM: Artificial Sequence
<220> FEATURE:
<223> OTHER INFORMATION: monoclonal antibody fragment

<400> SEQUENCE: 8

```
Ile Arg Thr Lys Pro Asn Asp Tyr Ala Thr
1               5                   10
```

<210> SEQ ID NO 9

```
<211> LENGTH: 8
<212> TYPE: PRT
<213> ORGANISM: Artificial Sequence
<220> FEATURE:
<223> OTHER INFORMATION: monoclonal antibody fragment

<400> SEQUENCE: 9

Thr Ala Phe Thr Glu Pro Asp Tyr
1               5

<210> SEQ ID NO 10
<211> LENGTH: 6
<212> TYPE: PRT
<213> ORGANISM: Artificial Sequence
<220> FEATURE:
<223> OTHER INFORMATION: monoclonal antibody fragment

<400> SEQUENCE: 10

Glu Leu Ser Lys Thr Tyr
1               5

<210> SEQ ID NO 11
<211> LENGTH: 3
<212> TYPE: PRT
<213> ORGANISM: Artificial Sequence
<220> FEATURE:
<223> OTHER INFORMATION: monoclonal antibody fragment

<400> SEQUENCE: 11

Lys Asp Ser
1

<210> SEQ ID NO 12
<211> LENGTH: 11
<212> TYPE: PRT
<213> ORGANISM: Artificial Sequence
<220> FEATURE:
<223> OTHER INFORMATION: monoclonal antibody fragment

<400> SEQUENCE: 12

Leu Ser Thr Tyr Ser Asp Asp Asn Leu Pro Val
1               5                   10

<210> SEQ ID NO 13
<211> LENGTH: 8
<212> TYPE: PRT
<213> ORGANISM: Artificial Sequence
<220> FEATURE:
<223> OTHER INFORMATION: monoclonal antibody fragment

<400> SEQUENCE: 13

Gly Phe Thr Phe Ser Asn Ala Trp
1               5

<210> SEQ ID NO 14
<211> LENGTH: 10
<212> TYPE: PRT
<213> ORGANISM: Artificial Sequence
<220> FEATURE:
<223> OTHER INFORMATION: monoclonal antibody fragment

<400> SEQUENCE: 14

Ile Lys Ala Lys Ser Asn Asn Tyr Ala Thr
1               5                   10

<210> SEQ ID NO 15
<211> LENGTH: 8
```

```
<212> TYPE: PRT
<213> ORGANISM: Artificial Sequence
<220> FEATURE:
<223> OTHER INFORMATION: monoclonal antibody fragment

<400> SEQUENCE: 15

Leu Tyr Gly Tyr Tyr Phe Asp Tyr
1               5

<210> SEQ ID NO 16
<211> LENGTH: 11
<212> TYPE: PRT
<213> ORGANISM: Artificial Sequence
<220> FEATURE:
<223> OTHER INFORMATION: monoclonal antibody fragment

<400> SEQUENCE: 16

Gln Ser Leu Ile His Ser Asn Gly Asn Thr Tyr
1               5                   10

<210> SEQ ID NO 17
<211> LENGTH: 3
<212> TYPE: PRT
<213> ORGANISM: Artificial Sequence
<220> FEATURE:
<223> OTHER INFORMATION: Antibody CDR

<400> SEQUENCE: 17

Arg Ile Ser
1

<210> SEQ ID NO 18
<211> LENGTH: 9
<212> TYPE: PRT
<213> ORGANISM: Artificial Sequence
<220> FEATURE:
<223> OTHER INFORMATION: Antibody CDR

<400> SEQUENCE: 18

Leu Gln Gly Thr His Leu Pro Phe Thr
1               5

<210> SEQ ID NO 19
<211> LENGTH: 120
<212> TYPE: PRT
<213> ORGANISM: Artificial Sequence
<220> FEATURE:
<223> OTHER INFORMATION: monoclonal antibody fragment

<400> SEQUENCE: 19

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Arg Asn
            20                  25                  30

Asn Val His Trp Val Arg Gln Pro Pro Gly Lys Gly Leu Glu Trp Met
        35                  40                  45

Gly Arg Met Arg Tyr Asn Gly Asp Thr Ser Tyr Asn Ser Ala Leu Lys
    50                  55                  60

Ser Arg Leu Ser Ile Ser Arg Asp Thr Ser Lys Asn Gln Val Phe Leu
65                  70                  75                  80

Lys Met Asn Ser Leu Gln Ile Asp Asp Thr Gly Thr Tyr Tyr Cys Ser
                85                  90                  95

Arg Glu Gly Tyr Tyr Asp Gly Tyr Tyr Pro Asp Tyr Trp Gly Gln
            100                 105                 110
```

Gly Val Met Val Thr Val Ser Ser
        115                 120

<210> SEQ ID NO 20
<211> LENGTH: 111
<212> TYPE: PRT
<213> ORGANISM: Artificial Sequence
<220> FEATURE:
<223> OTHER INFORMATION: monoclonal antibody fragment

<400> SEQUENCE: 20

Ser Val Thr Ser Tyr Glu Leu Ile Gln Pro Pro Ser Ala Ser Val Thr
1               5                   10                  15

Leu Glu Asn Thr Val Ser Ile Thr Cys Ser Gly Asp Glu Leu Ser Asn
            20                  25                  30

Lys Tyr Ala His Trp Tyr Gln Gln Lys Pro Asp Lys Thr Ile Leu Glu
        35                  40                  45

Val Met Tyr Lys Asp Ser Glu Arg Pro Ser Gly Ile Ser Asp Arg Phe
    50                  55                  60

Ser Gly Ser Ser Ser Gly Thr Thr Ala Ile Leu Thr Ile Arg Asp Ala
65                  70                  75                  80

Gln Ala Glu Asp Glu Ala Asp Tyr Tyr Cys Leu Ser Thr Tyr Ser Asp
                85                  90                  95

Asp Asp Leu Pro Val Phe Gly Gly Gly Thr Lys Leu Thr Val Leu
            100                 105                 110

<210> SEQ ID NO 21
<211> LENGTH: 8
<212> TYPE: PRT
<213> ORGANISM: Artificial Sequence
<220> FEATURE:
<223> OTHER INFORMATION: monoclonal antibody fragment

<400> SEQUENCE: 21

Gly Phe Ser Leu Thr Arg Asn Asn
1               5

<210> SEQ ID NO 22
<211> LENGTH: 7
<212> TYPE: PRT
<213> ORGANISM: Artificial Sequence
<220> FEATURE:
<223> OTHER INFORMATION: monoclonal antibody fragment

<400> SEQUENCE: 22

Met Arg Tyr Asn Gly Asp Thr
1               5

<210> SEQ ID NO 23
<211> LENGTH: 14
<212> TYPE: PRT
<213> ORGANISM: Artificial Sequence
<220> FEATURE:
<223> OTHER INFORMATION: monoclonal antibody fragment

<400> SEQUENCE: 23

Ser Arg Glu Gly Tyr Tyr Asp Gly Thr Tyr Tyr Pro Asp Tyr
1               5                   10

<210> SEQ ID NO 24
<211> LENGTH: 9
<212> TYPE: PRT
<213> ORGANISM: Artificial Sequence

```
<220> FEATURE:
<223> OTHER INFORMATION: monoclonal antibody fragment

<400> SEQUENCE: 24

Ser Gly Asp Glu Leu Ser Asn Lys Tyr
1               5

<210> SEQ ID NO 25
<211> LENGTH: 3
<212> TYPE: PRT
<213> ORGANISM: Artificial Sequence
<220> FEATURE:
<223> OTHER INFORMATION: monoclonal antibody fragment

<400> SEQUENCE: 25

Lys Asp Ser
1

<210> SEQ ID NO 26
<211> LENGTH: 11
<212> TYPE: PRT
<213> ORGANISM: Artificial Sequence
<220> FEATURE:
<223> OTHER INFORMATION: monoclonal antibody fragment

<400> SEQUENCE: 26

Leu Ser Thr Tyr Ser Asp Asp Asp Leu Pro Val
1               5                   10
```